United States Patent
Lu et al.

(10) Patent No.: US 10,265,288 B2
(45) Date of Patent: *Apr. 23, 2019

(54) METHODS AND COMPOSITIONS FOR THE TREATMENT OF PROLIFERATIVE DISORDERS

(71) Applicant: Beth Israel Deaconess Medical Center, Inc., Boston, MA (US)

(72) Inventors: Kun Ping Lu, Newton, MA (US); Shuo Wei, Chestnut Hill, MA (US); Xiao Zhen Zhou, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/334,052

(22) Filed: Jul. 17, 2014

(65) Prior Publication Data

US 2015/0044278 A1    Feb. 12, 2015

Related U.S. Application Data

(63) Continuation of application No. 14/004,759, filed as application No. PCT/US2012/029077 on Mar. 14, 2012.

(60) Provisional application No. 61/452,357, filed on Mar. 14, 2011.

(51) Int. Cl.

| | |
|---|---|
| *A61K 39/395* | (2006.01) |
| *A61K 31/203* | (2006.01) |
| *A61K 45/06* | (2006.01) |
| *A61K 31/436* | (2006.01) |
| *A61K 31/11* | (2006.01) |
| *A61K 31/232* | (2006.01) |
| *A61K 31/337* | (2006.01) |
| *A61K 31/4418* | (2006.01) |
| *A61K 31/475* | (2006.01) |
| *A61K 31/704* | (2006.01) |
| *A61K 31/7064* | (2006.01) |

(52) U.S. Cl.
CPC ............ *A61K 31/203* (2013.01); *A61K 31/11* (2013.01); *A61K 31/232* (2013.01); *A61K 31/337* (2013.01); *A61K 31/436* (2013.01); *A61K 31/4418* (2013.01); *A61K 31/475* (2013.01); *A61K 31/704* (2013.01); *A61K 31/7064* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,952,467 A | 9/1999 | Hunter et al. | |
| 5,972,697 A | 10/1999 | Hunter et al. | |
| 6,462,173 B1 | 10/2002 | Lu et al. | |
| 6,495,376 B1 | 12/2002 | Lu et al. | |
| 6,596,848 B1 | 7/2003 | Hunter et al. | |
| 6,764,698 B1* | 7/2004 | Byun et al. | 424/489 |
| 7,125,677 B2 | 10/2006 | Hunter et al. | |
| 7,125,955 B2 | 10/2006 | Hunter et al. | |
| 7,148,003 B2 | 12/2006 | Hunter et al. | |
| 7,161,060 B1 | 1/2007 | Duff et al. | |
| 7,164,012 B2 | 1/2007 | Hunter et al. | |
| 7,175,830 B2 | 2/2007 | Collins et al. | |
| 8,129,131 B2* | 3/2012 | Lu | G01N 33/574 |
| | | | 435/7.23 |
| 8,258,099 B2 | 9/2012 | Lu et al. | |
| 2002/0025521 A1 | 2/2002 | Lu et al. | |
| 2002/0106348 A1* | 8/2002 | Huang et al. | 424/85.1 |
| 2004/0176912 A1 | 9/2004 | Sowadski et al. | |
| 2005/0159485 A1 | 7/2005 | Jost-Price et al. | |
| 2005/0239095 A1 | 10/2005 | Lu et al. | |
| 2006/0018899 A1 | 1/2006 | Kao et al. | |
| 2006/0074222 A1 | 4/2006 | Lu et al. | |
| 2008/0118505 A1 | 5/2008 | Tedder | |
| 2008/0214470 A1 | 9/2008 | Lu et al. | |
| 2008/0248043 A1 | 10/2008 | Babcook et al. | |
| 2009/0258352 A1 | 10/2009 | Lu et al. | |
| 2009/0318391 A1* | 12/2009 | Ben-Sasson | A61K 31/196 |
| | | | 514/110 |

(Continued)

FOREIGN PATENT DOCUMENTS

| | | |
|---|---|---|
| WO | WO-97/17986 A1 | 5/1997 |
| WO | WO-99/09969 A1 | 3/1999 |

(Continued)

OTHER PUBLICATIONS

Wulf et al., "Pin 1 is overexpressed in breast cancer and cooperates with Ras signaling in increasing the transcriptional acivity of c-Jun towards cyclin D1," The EMBO Journal vol. 20, No. 13, (2001).*
Hu et al., "Nanoparticle-assisted combination therapies for effective cancer treatment," Therapeutic Delivery (2010) 1(2), 323-334.*
Kim et al., "Controlled Release of All-Trans-Retinoic Acid from PEGylated Gelatin nanoparticles by Enzymatic Degradation," Biotechnol. Bioprocess. Eng. 1999, 4, 215-218.*
Gianni et al., "Inhibition of the Peptidyl-Prolyl-Isomerase Pin1 Enhances the Responses of Acute Myeloid Leukemia Cells to Retinoic Acid via Stabilization of RARα and PML-RARα," Cancer Res 2009; 69:(3), Feb. 1, 2009.*
Bao et al., "Prevalent overexpression of prolyl isomerase Pin1 in human cancers," Am J Pathol. 164(5):1727-37 (2004).

(Continued)

*Primary Examiner* — Jared Barsky
(74) *Attorney, Agent, or Firm* — Clark & Elbing LLP

(57) ABSTRACT

The invention features methods of treating a proliferative disorder characterized by elevated Pin1 marker levels and/or reduced Pin1 Ser71 phosphorylation in a subject by administering a retinoic acid compound. Additionally, the invention features methods of treating proliferative disorders (e.g., proliferative disorders characterized by elevated Pin1 marker levels) by administering a retinoic acid compound in combination with another anti-proliferative compound. Finally, the invention also features methods including high-throughput screens for discovering and validating Pin1 inhibitors.

19 Claims, 17 Drawing Sheets

(56) References Cited

U.S. PATENT DOCUMENTS

| | | | |
|---|---|---|---|
| 2010/0010084 A1* | 1/2010 | Yu | 514/534 |
| 2010/0278832 A1 | 11/2010 | Kamogawa et al. | |
| 2011/0104756 A1 | 5/2011 | Rodriguez et al. | |
| 2012/0183560 A1 | 7/2012 | Akassoglou | |
| 2013/0028900 A1 | 1/2013 | Lu et al. | |
| 2014/0086909 A1 | 3/2014 | Lu et al. | |
| 2014/0219957 A1 | 8/2014 | Lu et al. | |
| 2014/0242100 A1 | 8/2014 | Lu et al. | |

FOREIGN PATENT DOCUMENTS

| | | |
|---|---|---|
| WO | WO-02/065091 A2 | 8/2002 |
| WO | WO-02/092765 A2 | 11/2002 |
| WO | WO-2004/016751 A2 | 2/2004 |
| WO | WO-2004/101745 A2 | 11/2004 |
| WO | WO-2005/027727 A2 | 3/2005 |
| WO | WO-2005/105058 A1 | 11/2005 |
| WO | WO-2009/003096 A2 | 12/2008 |
| WO | WO-2009/146218 A2 | 12/2009 |
| WO | WO-2012/125724 A1 | 9/2012 |
| WO | WO-2013/185055 A1 | 12/2013 |
| WO | WO-2014/152157 A2 | 9/2014 |
| WO | WO-2016/011268 A1 | 1/2016 |

OTHER PUBLICATIONS

Bartkova et al., "Cyclin D1 protein expression and function in human breast cancer," Int J Cancer. 57(3):353-61 (1994).
Gillet et al., "Amplification and overexpression of cyclin D1 in breast cancer detected by immunohistochemical staining," Cancer Res. 54(7):1812-7 (1994).
Arrieta et al., "Randomized phase II trial of All-trans-retinoic acid with chemotherapy based on paclitaxel and cisplatin as first-line treatment in patients with advanced non-small-cell lung cancer," J Clin Oncol. 28(21):3463-71 (2010).
Budd et al., "Phase I/II trial of all-trans retinoic acid and tamoxifen in patients with advanced breast cancer," Clin Cancer Res. 4(3):635-42 (1998).
Connolly et al., "Molecular pathways: current role and future directions of the retinoic acid pathway in cancer prevention and treatment," Clin Cancer Res. 19(7):1651-9 (2013).
Decensi et al., "Randomized double-blind 2 × 2 trial of low-dose tamoxifen and fenretinide for breast cancer prevention in high-risk premenopausal women," J Clin Oncol. 27(23):3749-56 (2009).
Ramlau et al., "Randomized phase III trial comparing bexarotene (L1069-49)/cisplatin/vinorelbine with cisplatin/vinorelbine in chemotherapy-naive patients with advanced or metastatic non-small-cell lung cancer: SPIRIT I," J Clin Oncol. 26(11):1886-92 (2008).

International Search Report and Written Opinion for International Application No. PCT/US15/40774, dated Oct. 23, 2015 (13 pages).
International Preliminary Report on Patentability for International Application No. PCT/US15/040774, dated Jan. 17, 2017 (6 pages).
International Preliminary Report on Patentability for International Application No. PCT/US12/029077, dated Sep. 17, 2013 (6 pages).
Lu et al., "Prolyl isomerase Pin1 in cancer," Cell Res. 24(9):1033-49 (2014).
Lu et al., "The prolyl isomerase PIN1: a pivotal new twist in phosphorylation signalling and disease," Nat Rev Mol Cell Biol. 8(11):904-16 (2007).
Wei et al., "Active Pin1 is a key target of all-trans retinoic acid in acute promyelocytic leukemia and breast cancer," Nat Med. 21(5):457-66 (2015).
Zhou et al., "The isomerase PIN1 controls numerous cancer-driving pathways and is a unique drug target," Nat Rev Cancer. 16(7):463-78 (2016). (16 pages).
Liao et al., "Chemical or genetic Pin1 inhibition exerts potent anticancer activity against hepatocellular carcinoma by blocking multiple cancer-driving pathways," Sci Rep. 7:43639; DOI: 10.1038/srep43639 (2017) (11 pages).
U.S. Appl. No. 61/968,862, Lu et al.
Esnault et al., "Pin1 modulates the type 1 immune response," PLoS One. 2(2):e226 (2007).
Gianni et al., "Inhibition of the peptidyl-prolyl-isomerase Pin1 enhances the responses of acute myeloid leukemia cells to retinoic acid via stabilization of RARalpha and PML-RARalpha," Cancer Res. 69(3):1016-26 (2009).
International Search Report and Written Opinion for International Application No. PCT/US14/027017, dated Oct. 28, 2014 (19 pages).
International Search Report and Written Opinion for International Application No. PCT/US2012/029077, dated Jul. 18, 2012 (8 pages).
International Search Report for International Application No. PCT/US2012/039850, dated Oct. 3, 2012 (3 pages).
Jeong et al., "Novel role of Pin1 induction in type II collagen-mediated rheumatoid arthritis," J Immunol. 183(10):6689-97 (2009).
Lam et al., "Prolyl isomerase Pin1 is highly expressed in Her2-positive breast cancer and regulates erbB2 protein stability," Mol Cancer 7(91):1-12 (2008).
Nakamura, et al. "Proline isomer-specific antibodies reveal the early pathogenic tau conformation in Alzheimer's disease" Cell. 149(1):232-44 (2012).
Office Action for U.S. Appl. No. 14/334,052, dated Nov. 20, 2014 (21 pages).
Written Opinion of the International Searching Authority for International Application No. PCT/US2012/039850, dated Oct. 3, 2012 (5 pages).

* cited by examiner

All-trans-retinoic acid (ATRA)

13-cis-retinoic acid (13cRA)

METHODS AND COMPOSITIONS FOR THE TREATMENT OF PROLIFERATIVE DISORDERS

CROSS-REFERENCE TO RELATED APPLICATIONS

This application is a continuation of U.S. application Ser. No. 14/004,759, filed Nov. 25, 2013, which is the U.S. National Stage of International Application No. PCT/US2012/029077, filed Mar. 14, 2012, which claims benefit of U.S. Provisional Application No. 61/452,357, filed Mar. 14, 2011.

STATEMENT AS TO FEDERALLY SPONSORED RESEARCH

This invention was made with government support under grants GM058556, AG017870, and CA122434 awarded by NIH. The government has certain rights in the invention.

FIELD OF THE INVENTION

In general, this invention relates to the treatment of proliferative disorders (e.g., proliferative disorders characterized by elevated Pin1 marker levels) with retinoic acid compounds.

BACKGROUND OF THE INVENTION

The increased number of cancer cases reported in the United States, and, indeed, around the world, is a major concern. Currently there are only a handful of detection and treatment methods available for some specific types of cancer, and these provide no absolute guarantee of success. In order to be most effective, these treatments require not only an early detection of the malignancy, but a reliable assessment of the severity of the malignancy.

It is apparent that the complex process of tumor development and growth must involve multiple gene products. It is therefore important to define the role of specific genes involved in tumor development and growth and identify those genes and gene products that can serve as targets for the diagnosis, prevention, and treatment of cancers.

In the realm of cancer therapy, it often happens that a therapeutic agent that is initially effective for a given patient becomes, over time, ineffective or less effective for that patient. The very same therapeutic agent may continue to be effective over a long period of time for a different patient. Further, a therapeutic agent that is effective, at least initially, for some patients can be completely ineffective or even harmful for other patients. Accordingly, it would be useful to identify genes and/or gene products that represent prognostic genes with respect to a given therapeutic agent or class of therapeutic agents. It then may be possible to determine which patients will benefit from particular therapeutic regimen and, importantly, determine when, if ever, the therapeutic regime begins to lose its effectiveness for a given patient. The ability to make such predictions would make it possible to discontinue a therapeutic regime that has lost its effectiveness well before its loss of effectiveness becomes apparent by conventional measures.

Recent advances in the understanding of molecular mechanisms of oncogenesis have led to exciting new drugs that target specific molecular pathways. These drugs have transformed cancer treatments, especially for those caused by some specific oncogenic events, such as Herceptin for breast cancer, caused by HER2/Neu, and Gleevec for chronic myelogenous leukemia caused by Bcr-Abl. However, it has been increasingly evident that, in many individual tumors, there are a large number of mutated genes that disrupt multiple interactive and/or redundant pathways. Thus, intervening in a single pathway may not be effective. Furthermore, cancer resistance to molecularly targeted drugs can develop through secondary target mutation or compensatory activation of alternative pathways, so-called "oncogenic switching." Thus, a major challenge remains how to simultaneously inhibit multiple oncogenic pathways either using a combination of multiple drugs, with each acting on a specific pathway, or using a single drug that concurrently blocks multiple pathways. The results disclosed herein suggest that Pin1 inhibitors might have a major impact on treating cancers, especially aggressive and/or drug-resistant cancers.

We and others have shown that Pin1 is prevalently overexpressed in human cancers and that high Pin1 marker levels correlate with poor clinical outcome in many cancers. In contrast, the Pin1 polymorphism that reduces Pin1 expression is associated with reduced cancer risk in humans. Significantly, Pin1 activates at least 19 oncogenes/growth enhancers, including β-catenin, cyclin D1, NF-κB, c-Jun, c-fos, AKT, A1B1, HER2/Neu, MCl-1, Notch, Raf-1, Stat3, c-Myb, Hbx, Tax, and v-rel, and also inactivates at least 12 tumor suppressors/growth inhibitors, including PML, SMRT, FOXOs, RARα, and Smad (FIGS. 1A and 1B). Whereas Pin1 overexpression causes cell transformation and tumorigenesis, Pin1 knockdown inhibits cancer cell growth in cell cultures and mice. Pin1-null mice are highly resistant to tumorigenesis induced either by oncogenes such as activated Ras or HER2/Neu, or tumor suppressors such as p53. Thus, Pin1 inhibitors might have the desired property to suppress numerous oncogenic pathways simultaneously for treating cancers, especially those aggressive and/or drug-resistant cancers.

SUMMARY OF THE INVENTION

In one aspect, the invention provides a method of treating a proliferative disease in a subject by administering a retinoic acid compound (e.g., a deuterated compound) to the subject in an amount sufficient to treat the subject, wherein the subject is determined to have elevated levels of a Pin1 marker (e.g., Ser71 phosphorylation) prior to the administration.

In another aspect, the invention features a method of treating a proliferative disease in a subject by determining Pin1 marker levels (e.g., reduced Ser71 phosphorylation) in a sample (e.g., tumor samples, blood, urine, biopsies, lymph, saliva, phlegm, and pus) from the subject and administering a retinoic acid compound to the subject if sample is determined to have elevated Pin1 marker levels.

In any of the foregoing aspects, the method can also include the administration of a second anti-proliferative compound (e.g., at a low dosage) or anti-cancer compound (e.g., an anti-angiogenic compound). The second compound can be administered separately, or in a single formulation with, the retinoic acid compound. The second anti-proliferative compound can be, e.g., MK-2206, ON 013105, RTA 402, BI 2536, Sorafenib, ISIS-STAT3Rx, a microtubule inhibitor, a topoisomerase inhibitor, a platin, an alkylating agent, an anti-metabolite, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalan, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and/or vinorelbine. Additionally, or alternatively, any of the foregoing methods can include determining Pin1 marker levels in the sample after the administration of a retinoic acid compound.

In any of the foregoing aspects, the retinoic acid compound may selected from 13-cis-retinoic acid, all-trans-retinoic acid, retinol, retinyl acetate, retinal, AC-55649, acitretin or any of the compounds listed in FIG. 2A, FIG. 2B, FIG. 10A, FIG. 10D, and Table 1.

The elevated Pin1 marker level of any of the foregoing methods can be due to, e.g., an inherited trait or a somatic mutation.

The proliferative disorder of any of the foregoing methods can be, e.g., leukemias, polycythemia vera, lymphomas, Waldenstrom's macroglobulinemia, heavy chain disease, and solid tumors. Specifically, the proliferative disorder can be e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemi), Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

The invention also features a method for identifying a Pin1 ligand including: (i) incubating Pin1 protein with a fluorescently labeled probe (e.g., HF488-FP or FITC-FP labeled peptide probes), forming a Pin1-probe complex; (ii) adding a test compound to the incubation; and (iii) determining whether any substantial portion of the probe is displaced from the Pin1-probe complex by the test compound, such displacement indicating that the test compound is a Pin1 ligand. The invention also features a method for identifying a Pin1 modulating compound including: (i) incubating human-derived cancer cells (e.g., breast cancer cells) that have Neu/Erb2 gene amplification; (ii) applying a test compound to the cell; and (iii) determining whether Neu/Erb2 overexpression is reduced, wherein reduction of Neu/Erb2 overexpression indicates that the test compound is a Pin1 modulating compound.

By the term "proliferative disorder" is meant a disorder characterized by inappropriate accumulation of a cell population in a tissue (e.g., by abnormal cell growth). This inappropriate accumulation may be the result of a genetic or epigenetic variation that occurs in one or more cells of the cell population. This genetic or epigenetic variation causes the cells of the cell population to grow faster, die slower, or differentiate slower than the surrounding, normal tissue. The cell population includes cells of hematopoietic, epithelial, endothelial, or solid tissue origin.

As used herein, the term "abnormal cell growth" is intended to include cell growth which is undesirable or inappropriate. Abnormal cell growth also includes proliferation which is undesirable or inappropriate (e.g., unregulated cell proliferation or undesirably rapid cell proliferation). Abnormal cell growth can be benign and result in benign masses of tissue or cells, or benign tumors. Many art-recognized conditions are associated with such benign masses or benign tumors including diabetic retinopathy, retrolental fibrioplasia, neovascular glaucoma, psoriasis, angiofibromas, rheumatoid arthritis, hemangiomas, and Karposi's sarcoma. Abnormal cell growth can also be malignant and result in malignancies, malignant masses of tissue or cells, or malignant tumors. Many art-recognized conditions and disorders are associated with malignancies, malignant masses, and malignant tumors including cancer and carcinoma.

As used herein, the term "tumor" is intended to encompass both in vitro and in vivo tumors that form in any organ of the body. Tumors may be associated with benign abnormal cell growth (e.g., benign tumors) or malignant cell growth (e.g., malignant tumors). The tumors which are described herein are preferably sensitive to the Pin1 inhibitors of the present invention. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys.

As used herein, the term "Pin1 marker" refers to a marker which is capable of being indicative of Pin1 activity levels in a sample of the invention. Pin1 markers include nucleic acid molecules (e.g., mRNA, DNA) which corresponds to some or all of a Pin1 gene, peptide sequences (e.g., amino acid sequences) which correspond to some or all of a Pin1 protein, nucleic acid sequences which are homologous to Pin1 gene sequences, peptide sequences which are homologous to Pin1 peptide sequences, antibodies to Pin1 protein, substrates of Pin1 protein, binding partners of Pin1 protein, and activity of Pin1.

By "elevated levels of a Pin1 marker" is meant a level of Pin1 marker that is altered thereby indicating elevated Pin1 activity. "Elevated levels of a Pin1 marker" include levels at least 5%, 6%, 7%, 8%, 9%, 10%, 15%, 20%, 25%, 30%, 40%, 50%, 60%, 70%, 80%, 90%, 100%, 200%, 500%, 1000%, or greater than, or 5%, 6%, 7%, 8%, 9%, 10%, 15%, 20%, 25%, 30%, 40%, 50%, 60%, 70%, 80%, 90%, 100% less than the marker levels measured in a normal, disease fee subject or tissue.

By the term "retinoic acid compound" is meant a compound that is either (a) the diterpene retinoic acid, or a derivative thereof, or (b) a compound having the structure $R^1—Ar^1-L^1Ar^2-L^2-C(=O)R^3$ (Formula (I)). Exemplary retinoic acid compounds described herein (including derivatives thereof) include the compounds identified in FIGS. 2A, 2B, 10A, 10D, and Table 1. The term "diterpene retinoic acid" encompasses any stereoisomer of retinoic acid (e.g., the retinoic acid may be in the all-trans configuration (ATRA) or one or more of the double bonds may be in the cis configuration (e.g., 13-cis retinoic acid (13cRA)). Derivatives of the diterpene retinoic acid include reduced forms such as retinal, retinol, and retinyl acetate. In Formula (I), each of $Ar^1$ and $Ar^2$ is, independently, optionally substituted aryl or an optionally substituted heteroaryl; $R^1$ is H, an optionally substituted alkyl group, an optionally substituted alkenyl group, or an optionally substituted alkynyl group; each of $L^1$ and $L^2$ is selected, independently from a covalent bond, an optionally substituted $C_{1-10}$ alkylene, an optionally substituted $C_{2-10}$ alkenylene (e.g., —CH=CH—, —COCH=CH—, —CH=CHCO—, a dienyl group, or a trienyl group), optionally substituted $C_{2-10}$ alkynylene (e.g., —C≡C—), or —(CHR$^4$)$_n$CONR$^5$—, —NR$^5$CO—, where n is 0 or 1, $R^4$ is H or OH, and $R^5$ is H or optionally substituted alkyl; and $R^3$ is H, OR$^4$ or N(R$^4$)$_2$, where each $R^4$ is selected, independently, from H, optionally substituted alkyl, or optionally substituted heteroalkyl.

Any of the chemical groups, functional groups, or substituents described herein may be deuterated if the chemical group, functional group, or substituent has —H. As used herein, when a particular position in a compound of this invention is designated as being "deuterated" or "having deuterium," it is understood that the position contains deuterium or includes deuterium (the element deuterium is represented by the letter "D" in chemical structures and formulas and indicated with a lower case "d" in chemical names, according to the Boughton system). When any of the position is deuterated, it is understood that the abundance of deuterium at that position is substantially greater than the natural abundance of deuterium, which is 0.015%. In certain embodiments, a composition of the invention has a minimum isotopic enrichment factor of at least 5 (0.075% deuterium incorporation), e.g., at least 10 (0.15% deuterium incorporation). In other embodiments, a composition has an isotopic enrichment factor of at least 50 (0.75% deuterium incorporation), at least 500 (7.5% deuterium incorporation), at least 2000 (30% deuterium incorporation), at least 3000 (45% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), or at least 6600 (99% deuterium incorporation).

As used herein, the term "isotopic enrichment factor" refers to the ratio of the isotopic abundance of a composition to the natural abundance of the specified isotope. For example, deuterium has a natural abundance of 0.015%. A compound with, for example, 45% deuterium incorporation at a specified position, has an isotopic enrichment factor of 3000 at that site relative to the natural abundance of deuterium.

TABLE 1

| List of compounds structurally similar to retinoic acid | | |
|---|---|---|
| CID | IUPAC | Other names |
| 444795 | (2E,4E,6E,8E)-3,7-dimethyl-9-(2,6,6-trimethylcyclohexen-1-yl)nona-2,4,6,8-tetraenoic acid | Retinoic acid; tretinoin; Vitamin A acid |
| 25145416 | (2Z,4E,6Z,8Z)-3,7-dimethyl-9-(2,6,6-trimethylcyclohexen-1-yl)nona-2,4,6,8-tetraenoic acid | |
| 23275881 | (2Z,4Z,6E,8Z)-3,7-dimethyl-9-(2,6,6-trimethylcyclohexen-1-yl)nona-2,4,6,8-tetraenoic acid | |
| 12358678 | (2E,4E,6E,8Z)-3,7-dimethyl-9-(2,6,6-trimethylcyclohexen-1-yl)nona-2,4,6,8-tetraenoic acid | CHEMBL44478; CHEBI:168407; AC-540 |
| 10881132 | (2Z,4Z,6E,8E)-3,7-dimethyl-9-(2,6,6-trimethylcyclohexen-1-yl)nona-2,4,6,8-tetraenoic acid | |
| 10638113 | (2E,4E,6E,8E)-3,7-dimethyl-9-(2,6,6-trimethylcyclohexen-1-yl)nona-2,4,6,8-tetraenoic acid | |
| 9861147 | (2E,4Z,6Z,8E)-3,7-dimethyl-9-(2,6,6-trimethylcyclohexen-1-yl)nona-2,4,6,8-tetraenoic acid | |
| 9796370 | (2E,4Z,6E,8E)-3,7-dimethyl-9-(2,6,6-trimethylcyclohexen-1-yl)nona-2,4,6,8-tetraenoic acid | 1tyr; (11Z)-retinoic acid; 11-cis-Retinoic acid |
| 6603983 | (2E,4Z,6Z,8Z)-3,7-dimethyl-9-(2,6,6-trimethylcyclohexen-1-yl)nona-2,4,6,8-tetraenoic acid | Tocris-0695; Lopac-R-2625; Lopac-R-3255 |
| 6419708 | (2Z,4E,6Z,8Z)-3,7-dimethyl-9-(2,6,6-trimethylcyclohexen-1-yl)nona-2,4,6,8-tetraenoic acid | 9,13-di-cis-RA; 9,13-Di-cis-retinoic acid; 9-cis,13-cis-Retinoic acid |
| 5282379 | (2Z,4E,6E,8E)-3,7-dimethyl-9-(2,6,6-trimethylcyclohexen-1-yl)nona-2,4,6,8-tetraenoic acid | Isotretinoin; 13-cis-Retinoic acid; Accutan |
| 449171 | (2E,4E,6Z,8E)-3,7-dimethyl-9-(2,6,6-trimethylcyclohexen-1-yl)nona-2,4,6,8-tetraenoic acid | Alitretinoin; Panretin; 9-CIS-RETINOIC ACID |
| 5538 | 3,7-dimethyl-9-(2,6,6-trimethylcyclohexen-1-yl)nona-2,4,6,8-tetraenoic acid | Spectrum_001676; SpecPlus_000696; AC1L1KKH |
| 54305566 | 2,4-dideuterio-7-methyl-3-(trideuteriomethyl)-9-(2,6,6-trimethylcyclohexen-1-yl)nona-2,4,6,8-tetraenoic acid | |
| 54305565 | 9-[3,3-dideuterio-6,6-dimethyl-2-(trideuteriomethyl)cyclohexen-1-yl]-3,7-dimethylnona-2,4,6,8-tetraenoic acid | |
| 10566385 | (2E,4E,6Z,8E)-7-methyl-3-(trideuteriomethyl)-9-(2,6,6-trimethylcyclohexen-1-yl)nona-2,4,6,8-tetraenoic acid | |

TABLE 1-continued

List of compounds structurally similar to retinoic acid

| CID | IUPAC | Other names |
|---|---|---|
| 10518761 | (2E,4E,6Z,8E)-7-methyl-9-(2,6,6-trimethylcyclohexen-1-yl)-3-(tritritiomethyl)nona-2,4,6,8-tetraenoic acid | |
| 10470200 | (2E,4Z,6Z,8E)-4,5-dideuterio-3,7-dimethyl-9-(2,6,6-trimethylcyclohexen-1-yl)nona-2,4,6,8-tetraenoic acid | |
| 10425032 | (2E,4E,6Z,8E)-4,5-dideuterio-3,7-dimethyl-9-(2,6,6-trimethylcyclohexen-1-yl)nona-2,4,6,8-tetraenoic acid | |
| 10357701 | (2E,4E,6Z,8E)-3,7-dimethyl-9-(2,6,6-trimethyl-4,5-ditritiocyclohexen-1-yl)nona-2,4,6,8-tetraenoic acid | |
| 10267048 | (2E,4E,6Z,8E)-3,7-dimethyl-9-(2,6,6-trimethylcyclohexen-1-yl)-4,5-ditritionona-2,4,6,8-tetraenoic acid | |
| 10086398 | (2Z,4Z,6Z,8E)-3,7-dimethyl-9-(2,6,6-trimethylcyclohexen-1-yl)-4,5-ditritionona-2,4,6,8-tetraenoic acid | |
| 10086397 | (2E,4E,6Z,8E)-3,7-dimethyl-9-(2,6,6-trimethyl-3,4-ditritiocyclohexen-1-yl)nona-2,4,6,8-tetraenoic acid | |
| 10063649 | (2E,4E,6Z,8E)-9-[2,6-dimethyl-6-(trideuteriomethyl)cyclohexen-1-yl]-3,7-dimethylnona-2,4,6,8-tetraenoic acid | |
| 10040620 | (2E,4E,6Z,8E)-9-(4,5-dideuterio-2,6,6-trimethylcyclohexen-1-yl)-3,7-dimethylnona-2,4,6,8-tetraenoic acid | |
| 10017935 | (2Z,4E,6E,8E)-3,7-dimethyl-9-(2,6,6-trimethylcyclohexen-1-yl)-4,5-ditritionona-2,4,6,8-tetraenoic acid | |
| 10017822 | (2E,4E,6Z,8E)-9-(3,4-dideuterio-2,6,6-trimethylcyclohexen-1-yl)-3,7-dimethylnona-2,4,6,8-tetraenoic acid | |
| 9995220 | (2E,4Z,6Z,8E)-3,7-dimethyl-9-(2,6,6-trimethylcyclohexen-1-yl)-4,5-ditritionona-2,4,6,8-tetraenoic acid | |
| 9972327 | (2Z,4Z,6E,8E)-3,7-dimethyl-9-(2,6,6-trimethylcyclohexen-1-yl)-4,5-ditritionona-2,4,6,8-tetraenoic acid | |
| 9972326 | (2E,4Z,6E,8E)-3,7-dimethyl-9-(2,6,6-trimethylcyclohexen-1-yl)-4,5-ditritionona-2,4,6,8-tetraenoic acid | |
| 9839397 | (2E,4E,6Z,8E)-3,7-dimethyl-9-(2,6,6-trimethylcyclohexen-1-yl)-5-tritionona-2,4,6,8-tetraenoic acid | |
| 6913160 | (2Z,4E,6Z,8E)-3,7-dimethyl-9-(2,6,6-trimethylcyclohexen-1-yl)-5-tritionona-2,4,6,8-tetraenoic acid | Retinoic-11-t acid; AC1OC7MJ; all-trans-(11-3H)-Retinoic acid |
| 6913136 | (2Z,4E,6Z,8E)-3,7-dimethyl-9-(2,6,6-trimethylcyclohexen-1-yl)-4,5-ditritionona-2,4,6,8-tetraenoic acid | AC1OC7KP; Retinoic-11,12-t2 acid; 11,12-3H-Retinoic acid |
| 6913131 | (2Z,4E,6Z,8E)-3,7-dimethyl-9-(2,6,6-trimethylcyclohexen-1-yl)-5,6-ditritionona-2,4,6,8-tetraenoic acid | AC1OC7KA; Retinoic-10,11-t2 acid; all-trans-(10,11-3H2)-Retinoic acid |
| 6439661 | (2Z,4E,6Z,8E)-3,7-dimethyl-9-(2,6,6-trimethylcyclohexen-1-yl)nona-2,4,6,8-tetraenoic acid | |
| 134262 | 3,7-dimethyl-9-(2,6,6-trimethylcyclohexen-1-yl)nona-2,4,6,8-tetraenoic acid | SHGAZHPCJJPHSC-SPLUINJESA-N; FDEFF7D13961B76 6CC9FE8A740623243 |
| 56684147 | (2E,6Z,8E)-3,7-dimethyl-9-(2,6,6-trimethylcyclohexen-1-yl)nona-2,6,8-trienoic acid | |
| 54219808 | 3,6,7-trimethyl-9-(2,6,6-trimethylcyclohexen-1-yl)nona-2,4,6,8-tetraenoic acid | |
| 53936974 | 3,7-dimethyl-9-(2,6,6-trimethylcyclohexen-1-yl)nona-2,6,8-trienoic acid | |
| 53740187 | 3,7-dimethyl-9-(2,6,6-trimethylcyclohexen-1-yl)nona-2,4,6-trienoic acid | |
| 44725022 | (Z)-3-[(E)-2-(2,6,6-trimethylcyclohexen-1-yl)ethenyl]hept-2-enoic acid | AC1Q2V68; (2Z)-3-[(E)-2-(2,6,6-trimethylcyclohex-1-en-1-yl)ethenyl]hept-2-enoic acid |
| 21590819 | (2Z,4E,8E)-3-methyl-7-methylidene-9-(2,6,6-trimethylcyclohexen-1-yl)nona-2,4,8-trienoic acid | CHEMBL182393 |
| 11738545 | (2E,4E,6E,8E)-3,7-dimethyl-9-(2,6,6-trimethylcyclohexen-1-yl)deca-2,4,6,8-tetraenoic acid | |
| 10518336 | (2E,4E,8E)-3-methyl-7-methylidene-9-(2,6,6-trimethylcyclohexen-1-yl)nona-2,4,8-trienoic acid | CHEMBL426963 |
| 10380944 | (2E,4E,6Z,8E)-3-ethyl-7-methyl-9-(2,6,6-trimethylcyclohexen-1-yl)nona-2,4,6,8-tetraenoic acid | |
| 10335106 | (2E,4E,6E)-3,7-dimethyl-9-(2,6,6-trimethylcyclohexen-1-yl)nona-2,4,6-trienoic acid | CHEMBL487208 |
| 10286439 | (2E,4E,6Z,8E)-7-ethyl-3-methyl-9-(2,6,6-trimethylcyclohexen-1-yl)nona-2,4,6,8-tetraenoic acid | |
| 10149682 | (2E,4E,6Z,8E)-3,6,7-trimethyl-9-(2,6,6-trimethylcyclohexen-1-yl)nona-2,4,6,8-tetraenoic acid | |

TABLE 1-continued

List of compounds structurally similar to retinoic acid

| CID | IUPAC | Other names |
|---|---|---|
| 10041353 | (2E,4E,6E,8E)-3-ethyl-7-methyl-9-(2,6,6-trimethylcyclohexen-1-yl)nona-2,4,6,8-tetraenoic acid | |
| 6439749 | (2E,4E,6E,8E)-9-(2-ethyl-6,6-dimethylcyclohexen-1-yl)-3,7-dimethylnona-2,4,6,8-tetraenoic acid | SRI 2712-24; 2,4,6,8-Nonatetracenoic acid, AC1NUZ8L |
| 5496917 | (2E,4Z,6E)-3,7-dimethyl-9-(2,6,6-trimethylcyclohexen-1-yl)nona-2,4,6-trienoic acid | |
| 5326825 | (2Z,4Z,6E)-3,7-dimethyl-9-(2,6,6-trimethylcyclohexen-1-yl)nona-2,4,6-trienoic acid | AC1NS159 |
| 4136524 | 3-[2-(2,6,6-trimethylcyclohexen-1-yl)ethenyl]hept-2-enoic acid | AC1N4YDA |
| 135317 | 9-(2-ethyl-6,6-dimethylcyclohexen-1-yl)-3,7-dimethylnona-2,4,6,8-tetraenoic acid | |
| 54525370 | 13-(2,6,6-trimethylcyclohexen-1-yl)trideca-2,4,6,8,10,12-hexaenoic acid | |
| 54472611 | 4,7-dimethyl-9-(2,6,6-trimethylcyclohexen-1-yl)nona-2,4,6,8-tetraenoic acid | |
| 54398880 | 3-methyl-5-[2-[2-(2,6,6-trimethylcyclohexen-1-yl)ethenyl]cyclopenten-1-yl]penta-2,4-dienoic acid | |
| 54044750 | 11-(2,6,6-trimethylcyclohexen-1-yl)undeca-2,4,6,8,10-pentaenoic acid | |
| 53876852 | 3,7-dimethyl-9-(2,4,6,6-tetramethylcyclohexen-1-yl)nona-2,4,6,8-tetraenoic acid | |
| 53790569 | 9-(2,6,6-trimethylcyclohexen-1-yl)nona-2,4,6,8-tetraenoic acid | |
| 53743104 | 5,9-dimethyl-11-(2,6,6-trimethylcyclohexen-1-yl)undeca-2,4,6,8,10-pentaenoic acid | |
| 44579060 | (2E,4E,6Z,8E)-9-(2-butyl-6,6-dimethylcyclohexen-1-yl)-3,7-dimethylnona-2,4,6,8-tetraenoic acid | CHEMBL518436 |
| 44393163 | (2Z,4E,8E)-7-methylidene-9-(2,6,6-trimethylcyclohexen-1-yl)nona-2,4,8-trienoic acid | |
| 25141345 | (2E,4E,6E,8E)-9-(2-butyl-6,6-dimethylcyclohexen-1-yl)-3,7-dimethylnona-2,4,6,8-tetraenoic acid | |
| 19609253 | (2E,4E)-3-methyl-5-[2-[(E)-2-(2,6,6-trimethylcyclohexen-1-yl)ethenyl]cyclopenten-1-yl]penta-2,4-dienoic acid | |
| 14731990 | (2E,4E,6E,8E)-7-methyl-9-(2,6,6-trimethylcyclohexen-1-yl)nona-2,4,6,8-tetraenoic acid | |
| 11141121 | (2E,4E,6E,8E)-4,7-dimethyl-9-(2,6,6-trimethylcyclohexen-1-yl)nona-2,4,6,8-tetraenoic acid | |
| 10712359 | (2E,4E,6Z)-3-methyl-7-[(E)-2-(2,6,6-trimethylcyclohexen-1-yl)ethenyl]undeca-2,4,6-trienoic acid | |
| 10474100 | (2E,4E,6E,8E,10E,12E)-3,7,11-trimethyl-13-(2,6,6-trimethylcyclohexen-1-yl)trideca-2,4,6,8,10,12-hexanoic acid | |
| 10426543 | (E,4E)-3-methyl-4-[3-[(E)-2-(2,6,6-trimethylcyclohexen-1-yl)ethenyl]cyclohex-2-en-1-ylidene]but-2-enoic acid | |
| 10358907 | (Z,4E)-3-methyl-4-[(4E)-3-methyl-4-[(2,6,6-trimethylcyclohexen-1-yl)methylidene]cyclohexa-2,5-dien-1-yl]methylidene) | |
| 10314319 | (2E,4E,6E,8E,10E)-5,9-dimethyl-11-(2,6,6-trimethylcyclohexen-1-yl)undeca-2,4,6,8,10-pentaenoic acid | CHEMBL225948 |
| 10286753 | (2E,4E,6Z,8E)-7-tert-butyl-3-methyl-9-(2,6,6-trimethylcyclohexen-1-yl)nona-2,4,6,8-tetraenoic acid | |
| 10266931 | (2E,4E,6Z)-3-methyl-7-[(E)-2-(2,6,6-trimethylcyclohexen-1-yl)ethenyl]deca-2,4,6-trienoic acid | CHEMBL507779 |
| 10125803 | (2E,4E,6Z)-3-methyl-7-[(E)-2-(2,6,6-trimethylcyclohexen-1-yl)ethenyl]deca-2,4,6-trienoic acid | |
| 10087786 | (Z,4E)-3-methyl-4-[3-[(E)-2-(2,6,6-trimethylcyclohexen-1-yl)ethenyl]cyclohex-2-en-1-ylidene]but-2-enoic acid | |
| 10015486 | (2E,4E,6E)-5-methyl-7-(2,6,6-trimethylcyclohexen-1-yl)hepta-2,4,6-trienoic acid | |
| 9929074 | (2E,4E,6E,8E)-3,7-dimethyl-9-(2,6,6-trimethylcyclohexen-1-yl)nona-2,4,6,8-tetraenoic acid | |
| 9860303 | (2E,4E,6E,8E)-9-(2,6,6-trimethylcyclohexen-1-yl)nona-2,4,6,8-tetraenoic acid | |
| 5355027 | (2E,4E)-3-methyl-5-(2,6,6-trimethylcyclohexen-1-yl)penta-2,4-dienoic acid | C15 acid; AC1NS6O9; NSC23978 |
| 167095 | 3-methyl-5-(2,6,6-trimethylcyclohexen-1-yl)penta-2,4-dienoic acid | AC1L4ZB4 |
| 56606832 | 3,7-dimethyl-9-(9,9,11-trimethylspiro[2.5]oct-10-en-10-yl)nona-2,4,6,8-tetraenoic acid | |
| 54548815 | 3,7,11,11-tetramethyldodeca-2,4-dienoic acid | |
| 54515105 | 7-methyl-3-[2-(2,6,6-trimethylcyclohexen-1-yl)ethenyl]nona-2,5-dienoic acid | YLWKTERFWUXEBW-UHFFFAOYSA-N; 005B26AC36D10A0C9DB5EF006864943F |
| 54358950 | 3-methyl-5-[2-[2-(2,6,6-trimethylcyclohexen-1-yl)ethenyl]cyclohepten-1-yl]penta-2,4-dienoic acid | |

TABLE 1-continued

List of compounds structurally similar to retinoic acid

| CID | IUPAC | Other names |
|---|---|---|
| 54353726 | 3,7,11,11-tetramethyltrideca-2,4-dienoic acid | |
| 54193713 | 3-methyl-5-[2-[2-(2,6,6-trimethylcyclohexen-1-yl)ethenyl]cycloocten-1-yl]penta-2,4-dienoic acid | |
| 53946778 | 2,3,7-trimethyl-9-(2,6,6-trimethylcyclohexen-1-yl)nona-2,4,6,8-tetraenoic acid | |
| 53944823 | 9-(6,6-dimethylcyclohexen-1-yl)-3,7-dimethylnona-2,4,6,8-tetraenoic acid | JAIGDKSXLVOFMH-UHFFFAOYSA-N; F42136BEED6C5A3745B9BA23356D7830 |
| 53921377 | 3-methyl-5-[2-[2-(2,6,6-trimethylcyclohexen-1-yl)ethenyl]cyclohexen-1-yl]penta-2,4-dienoic acid | |
| 44579100 | (2E,4E,6Z,8E)-9-[6,6-dimethyl-2-(2-methylpropyl)cyclohexen-1-yl]-3,7-dimethylnona-2,4,6,8-tetraenoic acid | CHEMBL476773 |
| 44579056 | (2E,4E,6E,8E)-9-[6,6-dimethyl-2-(2-methylpropyl)cyclohexen-1-yl]-3,7-dimethylnona-2,4,6,8-tetraenoic acid | CHEMBL476348 |
| 44314230 | (2Z,5E)-7-methyl-3-[(E)-2-(2,6,6-trimethylcyclohexen-1-yl)ethenyl]nona-2,5-dienoic acid | CHEMBL75548; CHEBI:220121 |
| 25011742 | (2E,8E)-3,7-dimethyl-9-(2,6,6-trimethylcyclohexen-1-yl)nona-2,8-dienoic acid | |
| 22646220 | (2E,4E,6E,8E)-2,3-dimethyl-9-(2,6,6-trimethylcyclohexen-1-yl)nona-2,4,6,8-tetraenoic acid | |
| 20830941 | (2E,4E,6E,8E)-2,3-dimethyl-9-(2,6,6-trimethylcyclohexen-1-yl)nona-2,4,6,8-tetraenoic acid | |
| 19609240 | (2E,4E)-3-methyl-5-[(1Z)-2-[(E)-2-(2,6,6-trimethylcyclohexen-1-yl)ethenyl]cycloocten-1-yl]penta-2,4-dienoic acid | |
| 18977383 | (2E,4E,6E,8E)-3,7-dimethyl-9-(2,5,6,6-tetramethylcyclohexen-1-yl)nona-2,4,6,8-tetraenoic acid | |
| 15125883 | (2Z,4E,6E,8E)-2,3,7-trimethyl-9-(2,6,6-trimethylcyclohexen-1-yl)nona-2,4,6,8-tetraenoic acid | |
| 15125882 | (2E,4E,6E,8E)-2,3,7-trimethyl-9-(2,6,6-trimethylcyclohexen-1-yl)nona-2,4,6,8-tetraenoic acid | CHEMBL153895; 14-methyl-all-trans-retinoic acid; LMPR01090034 |
| 11266097 | (2Z,4E,8E)-3-methyl-9-(2,6,6-trimethylcyclohexen-1-yl)nona-2,4,8-trien-6-ynoic acid | |
| 11000660 | (2E,4E,6Z,8E)-9-(6,6-dimethylcyclohexen-1-yl)-3,7-dimethylnona-2,4,6,8-tetraenoic acid | |
| 10733921 | (2E,4E,6Z)-7-(8,8-dimethyl-4,5,6,7-tetrahydro-3H-naphthalen-2-yl)-3-methylocta-2,4,6-trienoic acid | |
| 10636975 | (2E,4E,6E,8E)-9-(6,6-dimethylcyclohexen-1-yl)-3,7-dimethylnona-2,4,6,8-tetraenoic acid | |
| 10591236 | (2E,4E,6Z)-7-(4a,8-dimethyl-4,5,6,7-tetrahydro-3H-naphthalen-2-yl)-3-methylocta-2,4,6-trienoic acid | |
| 10404132 | (Z,4E)-3-methyl-4-[(4E)-3-methyl-4-[(2,6,6-trimethylcyclohexen-1-yl)methylidene]cyclohex-2-en-1-ylidene]but-2-enoic acid | |
| 10314318 | (E,4E)-3-methyl-4-[(4E)-3-methyl-4-[(2,6,6-trimethylcyclohexen-1-yl)methylidene]cyclohex-2-en-1-ylidene]but-2-enoic acid | |
| 10215224 | (2E,4E,6Z,8E)-3-methyl-7-propan-2-yl-9-(2,6,6-trimethylcyclohexen-1-yl)nona-2,4,6,8-tetraenoic acid | |
| 10193246 | (2E,4E)-3-methyl-6-[1-[(E)-2-(2,6,6-trimethylcyclohexen-1-yl)ethenyl]cyclopropyl]hexa-2,4-dienoic acid | |
| 9841547 | (2E,4E)-3-methyl-5-[2-[(E)-2-(2,6,6-trimethylcyclohexen-1-yl)ethenyl]cyclohepten-1-yl]penta-2,4-dienoic acid | |
| 9830767 | (2Z,4E,6Z,8E)-9-(6,6-dimethylcyclohexen-1-yl)-3,7-dimethylnona-2,4,6,8-tetraenoic acid | |
| 9819335 | (2E,4E)-3-methyl-5-[2-[(E)-2-(2,6,6-trimethylcyclohexen-1-yl)ethenyl]cyclohexen-1-yl]penta-2,4-dienoic acid | Ro 25-6603; 173792-73-9 |
| 56667667 | (2E,4E,6Z,8E)-3,7-dimethyl-9-(6-methyl-3-prop-1-en-2-ylcyclohexen-1-yl)nona-2,4,6,8-tetraenoic acid | CHEMBL455993; CHEMBL455994 |
| 54758572 | (2Z,4E,6Z,8E)-3,7-dimethyl-9-(2,6,6-trimethylcyclohexen-1-yl)nona-2,4,6,8-tetraenoate | 9-cis-Retinoate; CPD-13549 |
| 54426679 | 2,7-dimethyl-9-(2,6,6-trimethylcyclohexen-1-yl)nona-2,4,6,8-tetraenoic acid | |
| 54325149 | 6-chloro-3,7-dimethyl-9-(2,6,6-trimethylcyclohexen-1-yl)nona-2,4,6,8-tetraenoic acid | |
| 53702687 | 6-iodo-3,7-dimethyl-9-(2,6,6-trimethylcyclohexen-1-yl)nona-2,4,6,8-tetraenoic acid | |
| 29986894 | (2E,4Z,6E,8E)-3,7-dimethyl-9-(2,6,6-trimethylcyclohexen-1-yl)nona-2,4,6,8-tetraenoate | ZINC22066351 |
| 29927144 | (2E,4E,6E,8Z)-3,7-dimethyl-9-(2,6,6-trimethylcyclohexen-1-yl)nona-2,4,6,8-tetraenoate | ZINC21992287 |
| 24916820 | (2E,4E,6E)-3,7-dimethyl-9-(2,6,6-trimethylcyclohexen-1-yl)nona-2,4,6-trienoate | 2g78 |
| 24771817 | 3,7-dimethyl-9-(2,6,6-trimethylcyclohexen-1-yl)nona-2,4,6,8-tetraenoate | CHEBI:15036 |

TABLE 1-continued

List of compounds structurally similar to retinoic acid

| CID | IUPAC | Other names |
|---|---|---|
| 21917290 | (2E,4E,6E,8E)-9-(5-tert-butyl-2,6,6-trimethylcyclohexen-1-yl)-3,7-dimethylnona-2,4,6,8-tetraenoic acid | |
| 19609245 | (2E,4E,6E,8E)-6-chloro-3,7-dimethyl-9-(2,6,6-trimethylcyclohexen-1-yl)nona-2,4,6,8-tetraenoic acid | |
| 19609224 | (2E,4E,6E,8E)-6-iodo-3,7-dimethyl-9-(2,6,6-trimethylcyclohexen-1-yl)nona-2,4,6,8-tetraenoic acid | |
| 10924150 | (2E,4E,6Z,8E)-9-(2,6-dimethylcyclohexen-1-yl)-3,7-dimethylnona-2,4,6,8-tetraenoic acid | |
| 10613228 | (2E,4E,6E,8E)-9-(2,6-dimethylcyclohexen-1-yl)-3,7-dimethylnona-2,4,6,8-tetraenoic acid | |
| 10469989 | (2E,6Z,8E)-3,7-dimethyl-9-(2,6,6-trimethylcyclohexen-1-yl)nona-2,6,8-trien-4-ynoic acid | |
| 10334998 | (2E,4E)-3-methyl-5-[2-[(E)-2-(2,6,6-trimethylcyclohexen-1-yl)ethenyl]cyclopropyl]penta-2,4-dienoic acid | |
| 9904356 | (2Z,4E,6Z)-3,7-dimethyl-9-(2,6,6-trimethylcyclohexen-1-yl)nona-2,4,6-trien-8-ynoic acid | |
| 7364357 | (2E,4E,6Z,8E)-3,7-dimethyl-9-(2,6,6-trimethylcyclohexen-1-yl)nona-2,4,6,8-tetraenoate | AC1OKKW8; ZINC12661824; 13-cis-retinoate; ZINC03792789 |
| 7048538 | (2Z,4E,6E,8E)-3,7-dimethyl-9-(2,6,6-trimethylcyclohexen-1-yl)nona-2,4,6,8-tetraenoate | |
| 6440565 | 2E,4E,6E)-3,7-dimethyl-9-(2,6,6-trimethylcyclohexen-1-yl)nona-2,4,6-trien-8-ynoic acid | 7,8-Dehydroretinoic acid; 7,8-Didehydroretinoic acid |
| 6419707 | (2E,4E,6E,8E)-3,7-dimethyl-9-(2,6,6-trimethylcyclohexen-1-yl)nona-2,4,6,8-tetraenoate | Retinoate; all-trans-Retinoate; Tretinoine |
| 5771658 | (Z)-3-(2,6,6-trimethylcyclohexen-1-yl)prop-2-enoic acid | NSC-202789; AC1NY9IQ; NCGC00014560 |
| 5383969 | (E)-3-(2,6,6-trimethylcyclohexen-1-yl)prop-2-enoic acid | NSC202789; NSC-20278 |
| 5353358 | (2Z,4E)-3-methyl-6-(2,7,7-trimethyl-3-methylidene-1,4,5,6-tetrahydroinden-2-yl)hexa-2,4-dienoic acid | AC1NS43Q |
| 5289278 | (2E,4E)-3-methyl-6-[(2R)-2,7,7-trimethyl-3-methylidene-1,4,5,6-tetrahydroinden-2-yl]hexa-2,4-dienoic acid | NSC202789; 3-(2,6,6-trimethyl-1-cyclohexen-1-yl)acrylic acid; AC1L77HZ |
| 305742 | 3-(2,6,6-trimethylcyclohexen-1-yl)prop-2-enoic acid | NSC202789; 3-(2,6,6-trimethyl-1-cyclohexen-1-yl)acrylic acid; AC1L77HZ |
| 1851 | 3-methyl-6-(2,7,7-trimethyl-3-methylidene-1,4,5,6-tetrahydroinden-2-yl)hexa-2,4-dienoic acid | AC1L1CDO |
| 54399542 | 6-bromo-3,7-dimethyl-9-(2,6,6-trimethylcyclohexen-1-yl)nona-2,4,6,8-tetraenoic acid | |
| 54233476 | 3,7-dimethyl-5-oxo-9-(2,6,6-trimethylcyclohexen-1-yl)nona-2,6,8-trienoic acid | |
| 54033110 | 2,5,9-trimethyl-11-(2,6,6-trimethylcyclohexen-1-yl)undeca-2,4,6,8,10-pentaenoic acid | |
| 53936708 | 3-methyl-5-[2-[2-(2,6,6-trimethylcyclohexen-1-yl)ethynyl]cyclopenten-1-yl]penta-2,4-dienoic acid | |
| 44314320 | (2Z,4E)-3-methyl-5-[2-[(E)-2-(3,3,6,6-tetramethylcyclohexen-1-yl)ethenyl]cyclopropyl]penta-2,4-dienoic acid | CHEMBL73973; CHEBI:220303 |
| 44314319 | (2E,4E)-3-methyl-5-[2-[(E)-2-(3,3,6,6-tetramethylcyclohexen-1-yl)ethenyl]cyclopropyl]penta-2,4-dienoic acid | CHEMBL74331; CHEBI:220301 |
| 22373193 | (2E,4E)-3-methyl-5-[2-[2-(2,6,6-trimethylcyclohexen-1-yl)ethynyl]cyclopenten-1-yl]penta-2,4-dienoic acid | |
| 21145248 | (2Z,4E,6E,8E)-3,7-dimethyl-9-(2,6,6-trimethylcyclohexen-1-yl)nona-2,4,6,8-tetraenoic acid | |
| 20151571 | (2E,4E,6E,8E)-3,7-dimethyl-9-(2,6,6-trimethylcyclohexen-1-yl)nona-2,4,6,8-tetraenoic acid | |
| 19609231 | (2E,4E,6E,8E)-6-bromo-3,7-dimethyl-9-(2,6,6-trimethylcyclohexen-1-yl)nona-2,4,6,8-tetraenoic acid | |
| 16727824 | (2E,4E,6Z,8E)-3,7-dimethyl-9-(2,6,6-trimethylcyclohexen-1-yl)nona-2,4,6,8-tetraenoic acid | All-trans-Retinoic acid & 9-cis-Retinoic Acid |
| 11015604 | (2E,4E,6E,8E,10E,12E,14E,16E)-2,6,11,15-tetramethyl-17-(2,6,6-trimethylcyclohexen-1-yl)-3-tritioheptadeca-2,4,6,8-trimethylcyclyhexen-1-yl)-3-tritioheptadeca-2,4,6,8,10,12,14,16-octaenoic acid | |
| 10406618 | (2E,4Z,6E,8E,10E,12E)-2,7,11-trimethyl-13-(2,6,6-trimethylcyclohexen-1-yl)trideca-2,4,6,8,10,12-hexanoic acid | |
| 9976193 | (2E,4E,6E,8E,10E,12E)-2,7,11-trimethyl-13-(2,6,6-trimethylcyclohexen-1-yl)trideca-2,4,6,8,10,12-hexanoic acid | |

TABLE 1-continued

List of compounds structurally similar to retinoic acid

| CID | IUPAC | Other names |
|---|---|---|
| 9843074 | (2E,4E,6E)-3-methyl-7-(4,4,7,7-tetramethyl-2-pentyl-1,3,5,6-tetrahydroinden-2-yl)hepta-2,4,6-trienoic acid | |
| 6439881 | (2Z,4E,6Z,8E)-9-(3,3-difluoro-2,6,6-trimethylcyclohexen-1-yl)-3,7-dimethylnona-2,4,6,8-tetraenoic acid | DFRA; 4,4-Difluororetinoic acid; AC1O5SM |
| 6436320 | (2E,4E,6Z,8E,10E,12E,14E,16E)-2,6,11,15-tetramethyl-17-(2,6,6-trimethylcyclohexen-1-yl)heptadeca-2,4,6,8,10,12,14,16-octaenoic acid | AC1O5LFK; beta-apo-8'-Carotenoic acid; 8'-Apo-beta,psi-carotenoic acid |
| 5387557 | (2Z)-2-[5-(2,6,6-trimethylcyclohexen-1-yl)-3-[(E)-2-(2,6,6-trimethylcyclohexen-1-yl)ethenyl]cyclohexanoic acid | NSC624510; AC1NTSHG; AC1Q5T6Y |
| 5366642 | (2E,4E,6E,8E)-9-(3,3-difluoro-2,6,6-trimethylcyclohexen-1-yl)-3,7-dimethylnona-2,4,6,8-tetraenoic acid | 4,4-Difluororetinoic acid; AC1NSNWF; 4,4-Difluororetinoic acid (all-trans) |
| 361473 | 2-[5-(2,6,6-trimethylcyclohexen-1-yl)-3-[2-(2,6,6-trimethylcyclohexen-1-yl)ethenyl]cyclohex-2-en-1-yl)heptadeca-2,4,6,8,10,12,14,16-octaenoic acid | AC1L7IQC; NCI60_007432; 2-[5-(2,6,6-trimethylcyclohexen-1-yl)-3-[2-(2,6,6-trimethylcyclohexen-1-yl)ethenyl]cyclohex-2-en-1-ylidene]acetic acid |
| 146218 | 9-(3,3-difluoro-2,6,6-trimethylcyclohexen-1-yl)-3,7-dimethylnona-2,4,6,8-tetraenoic acid | |
| 56660872 | (2E,4E,6Z,8E)-3,7-dimethyl-9-(2-methyl-5-prop-1-en-2-ylcyclohexen-1-yl)nona-2,4,6,8-tetraenoic acid | CHEMBL457645; CHEMBL513434 |
| 54587023 | (2E,4E,6Z,8E)-3,7-dimethyl-9-[(3S,6R)-3-methyl-6-prop-1-en-2-ylcyclohexen-1-yl]nona-2,4,6,8-tetraenoic acid | CHEMBL1773351 |
| 54586043 | (2E,4E,6Z)-3-methyl-7-[(3R,6S)-3-methyl-6-propan-2-ylcyclohexen-1-yl]octa-2,4,6-trienoic acid | CHEMBL1773361 |
| 54310202 | 7-ethyl-3,11-dimethyltrideca-2,4-dienoic acid | |
| 54177995 | 8-(3-ethyl-2-propan-2-ylcyclohex-2-en-1-ylidene)-3,7-dimethylocta-2,4,6-trienoic acid | OZUTXDDSOLQKNK-UHFFFAOYSA-N; 982DADEA9DC5579A132BDF2AD7FA647A |
| 54012267 | 3,8,12-trimethyltrideca-2,4-dienoic acid | |
| 53787191 | 3,8,13-trimethyltetradeca-2,4-dienoic acid | |
| 53743194 | 4-methyl-6-(2,6,6-trimethylcyclohexen-1-yl)hex-2-enoic acid | |
| 53710521 | 3,7,13-trimethyltetradeca-2,4-dienoic acid | |
| 53707670 | 3,7-dimethyl-8-(3-methyl-2-propan-2-ylcyclohex-2-en-1-ylidene)octa-2,4,6-trienoic acid | BYHSFJNWVLBCIM-UHFFFAOYSA-N; 14B10A34153F37A66327788679FAC42F |
| 53666154 | 3,7,11-trimethyltrideca-2,4-dienoic acid | |
| 53438161 | 3,7,11-trimethyltetradeca-2,4-dienoic acid | |
| 53427754 | 7,7-dimethylicosa-2,4-dienoic acid | |
| 52952998 | (2E,4E,6Z,8E)-3,7-dimethyl-9-[(3R,6S)-3-methyl-6-prop-1-en-2-ylcyclohexen-1-yl]nona-2,4,6,8-tetraenoic acid | CHEMBL1773352 |
| 44631433 | (2Z,4E)-3-methyl-5-(2,2,4-trimethylcyclohex-3-en-1-yl)penta-2,4-dienoic acid | FZFFLFPGBIXCKI-STRRHFTISA- |
| 44291210 | (2Z,4Z,6Z,8E)-8-(3-ethyl-2-propan-2-ylcyclohex-2-en-1-ylidene)-3,7-dimethylocta-2,4,6-trienoic acid | CHEMBL43954 |
| 44290946 | (2E,4Z,6Z,8E)-8-(3-ethyl-2-propan-2-ylcyclohex-2-en-1-ylidene)-3,7-dimethylocta-2,4,6-trienoic acid | CHEMBL43833; CHEBI:167938 |
| 24845989 | sodium (2Z,4E,6Z,8E)-3,7-dimethyl-9-(2,6,6-trimethylcyclohexen-1-yl)nona-2,4,6,8-tetraenoate | LS-143475 |
| 23670222 | potassium (2E,4E,6E,8E)-3,7-dimethyl-9-(2,6,6-trimethylcyclohexen-1-yl)nona-2,4,6,8-tetraenoate | |
| 23665641 | sodium (2E,4E,6E,8E)-3,7-dimethyl-9-(2,6,6-trimethylcyclohexen-1-yl)nona-2,4,6,8-tetraenoate | Sodium retinoate; Retinoic acid, sodium salt; Vitamin A acid sodium sal |
| 23265304 | (2E,4E)-3-methyl-5-(2,2,4-trimethylcyclohex-3-en-1-yl)penta-2,4-dienoic acid | |
| 21437585 | (2E,4E)-3,8,12-trimethyltrideca-2,4-dienoic acid | |
| 21437539 | (2E,4E)-3,8,13-trimethyltetradeca-2,4-dienoic acid | |
| 21437504 | (2E,4E)-3,7,13-trimethyltetradeca-2,4-dienoic acid | |

TABLE 1-continued

List of compounds structurally similar to retinoic acid

| CID | IUPAC | Other names |
|---|---|---|
| 21158960 | (2E,4E)-7,7-dimethylicosa-2,4-dienoic acid | |
| 20270951 | (6E,8E)-2,7-dimethyl-9-(2,6,6-trimethylcyclohexen-1-yl)nona-2,3,6,8-tetraenoic acid | |
| 19609232 | (2E,4E)-3-methyl-5-[2-[(E)-2-(2,6,6-trimethylcyclohexen-1-yl)ethenyl]cyclohexen-1-yl]penta-2,4-dienoic acid | |
| 11130378 | (2E,4E,6E,8E)-3,7-dimethyl-9-(2,6,6-trimethylcyclohex-2-en-1-yl)nona-2,4,6,8-tetraenoic acid | |
| 11066537 | (2Z,4E,6E,8E)-3,7-dimethyl-9-(2,6,6-trimethylcyclohex-2-en-1-yl)nona-2,4,6,8-tetraenoic acid | |
| 10470917 | (2Z,4E,6Z,8E)-8-(3-ethyl-2-propan-2-ylcyclohex-2-en-1-ylidene)-3,7-dimethylocta-2,4,6-trienoic acid | |
| 10402558 | (2Z,4E,6E,8E)-3,7-dimethyl-8-(3-methyl-2-propan-2-ylcyclohex-2-en-1-ylidene)octa-2,4,6-trienoic acid | |
| 10357464 | (2E,4E,6Z,8E)-3,7-dimethyl-8-(3-methyl-2-propan-2-ylcyclohex-2-en-1-ylidene)octa-2,4,6-trienoic acid | |
| 10086191 | (2E,4E,6E,8E)-3,7-dimethyl-8-(3-methyl-2-propan-2-ylcyclohex-2-en-1-ylidene)octa-2,4,6-trienoic acid | CHEMBL333032; CHEBI:299410 |
| 10086189 | (2Z,4E,6Z,8E)-3,7-dimethyl-8-(3-methyl-2-propan-2-ylcyclohex-2-en-1-ylidene)octa-2,4,6-trienoic acid | |
| 9972952 | (2Z,4E,6E,8E)-8-(3-ethyl-2-propan-2-ylcyclohex-2-en-1-ylidene)-3,7-dimethylocta-2,4,6-trienoic acid | CHEMBL44582; CHEBI:168408 |
| 9972949 | (2E,4E,6Z,8E)-8-(3-ethyl-2-propan-2-ylcyclohex-2-en-1-ylidene)-3,7-dimethylocta-2,4,6-trienoic acid | |
| 9883342 | (2E,4E,6E,8E)-8-(3-ethyl-2-propan-2-ylcyclohex-2-en-1-ylidene)-3,7-dimethylocta-2,4,6-trienoic acid | CHEMBL46398; CHEBI:168441 |
| 5372326 | (E)-3-methyl-5-(2,6,6-trimethylcyclohexen-1-yl)pent-2-enoic acid | AC1NSY3I; 2-Pentenoic acid, 3-methyl-5-(2,6,6-trimethyl-1-cyclohexenyl); (E)-3-methyl-5-(2,6,6-trimethylcyclohexen-1-yl)pent-2-enoic acid |
| 445560 | (2E,4E,6Z,8E)-3,7-dimethyl-9-(2,6,6-trimethylcyclohex-2-en-1-yl)nona-2,4,6,8-tetraenoic acid | AC1L9I79 |
| 56667221 | (2E,4E,6Z,8E)-3,7-dimethyl-9-(3-methyl-6-propan-2-ylcyclohexen-1-yl)nona-2,4,6,8-tetraenoic acid | CHEMBL508378 |
| 54585066 | (2E,4E,6Z,8E)-3,7-dimethyl-9-[(1S,4R,5R)-4,6,6-trimethyl-3-bicyclo[3.1.1]hept-2-enyl]nona-2,4,6,8-tetraenoic acid | CHEMBL1773358 |
| 54585064 | (2E,4E,6Z,8E)-3,7-dimethyl-9-[(3R)-3-methyl-6-propan-2-ylidenecyclohexen-1-yl]nona-2,4,6,8-tetraenoic acid | CHEMBL1773355 |
| 54582176 | (2E,4E,6Z,8E)-3,7-dimethyl-9-[(3S)-3-methyl-6-propan-2-ylidenecyclohexen-1-yl]nona-2,4,6,8-tetraenoic acid | CHEMBL1773354 |
| 54581148 | (2E,4E,6Z,8E)-3,7-dimethyl-9-[(1R,2R,5S)-2-methyl-5-propan-2-yl-3-bicyclo[3.1.0]hex-3-enyl]nona-2,4,6,8-tetraenoic acid | CHEMBL1773360 |
| 54542310 | 3,4,4-trimethyltetradec-2-enoic acid | |
| 54521054 | 3,4,4-trimethyloctadec-2-enoic acid | |
| 54518673 | 3,7-dimethyl-9-(2,6,6-trimethyl-5-oxocyclohexen-1-yl)nona-2,4,6,8-tetraenoic acid | |
| 54348687 | 3,7,10,11-tetramethyldodeca-2,4-dienoic acid | |
| 54325421 | 3,4,4-trimethylheptadec-2-enoic acid | |
| 54316493 | 3,4,4-trimethylpentadec-2-enoic acid | |
| 54305044 | 2-ethyl-3,7-dimethyl-9-(2,6,6-trimethylcyclohexen-1-yl)nona-2,4,6,8-tetraenoic acid | |
| 54265680 | 3,7,11,15-tetramethylhexadeca-2,4-dienoic acid | |
| 54194359 | 3,7-dimethyl-9-(2,6,6-trimethyl-4-oxocyclohexen-1-yl)nona-2,4,6,8-tetraenoic acid | |
| 54170467 | 3,7,11,15-tetramethylhexadeca-2,4,6,14-tetraenoic acid | |
| 54167172 | 3,4,4-trimethylhexadec-2-enoic acid | |
| 54105865 | 3,7,7,11,11-pentamethyldodec-2-enoic acid | |
| 54064253 | 2-ethyl-5,9-dimethyl-3-(2,6,6-trimethylcyclohexen-1-yl)undeca-2,4,6,8,10-pentaenoic acid | |
| 53961371 | 3,7,11-trimethyldodeca-2,4,11-trienoic acid | |
| 53936602 | 9-[5-(2-cyclohexylethyl)-2,6,6-trimethylcyclohexen-1-yl]-3,7-dimethylnona-2,4,6,8-tetraenoic acid | |
| 53825233 | 3,7,11,15,19-pentamethylicosa-2,4,6,10,18-pentaenoic acid | |
| 53801569 | 3-methyl-5-[2-[2-(2,6,6-trimethylcyclohexen-1-yl)ethynyl]cyclohepten-1-yl]penta-2,4-dienoic acid | |
| 53725805 | 3,7-dimethyldodeca-2,4-dienoic acid | |
| 53700416 | 3,7,11,15-tetramethylhexadeca-2,4,6-trienoic acid | |
| 52953080 | (2E,4E,6Z,8E)-3,7-dimethyl-9-[(3S,6R)-3-methyl-6-propan-2-ylcyclohexen-1-yl]nona-2,4,6,8-tetraenoic acid | CHEMBL1773353 |
| 52952997 | (2E,4E,6Z,8E)-3,7-dimethyl-9-[(1R,4S,5S)-4,6,6-trimethyl-3-bicyclo[3.1.1]hept-2-enyl]nona-2,4,6,8-tetraenoic acid | CHEMBL1773357 |

TABLE 1-continued

List of compounds structurally similar to retinoic acid

| CID | IUPAC | Other names |
|---|---|---|
| 52921782 | (2E,5R,10E,12E)-3,5,15-trimethyl-7-methylidenehexadeca-2,10,12-trienoic acid | LMFA01020367; 16:3(2E,10E,12E)(3Me, 5Me[R],7My,15Me) |
| 46178652 | (2E,4E)-5-[(1R)-2,2-dimethyl-6-methylidenecyclohexyl]-3-methylpenta-2,4-dienoic acid | |
| 44579059 | (2E,4E,6Z,8E)-3,7-dimethyl-9-(2,2,6-trimethylcyclohexyl)nona-2,4,6,8-tetraenoic acid | CHEMBL451158 |
| 25147656 | (2E,4E,6Z,8E)-3,7-dimethyl-9-[(3R,6S)-3-methyl-6-propan-2-ylcyclohexen-1-yl]nona-2,4,6,8-tetraenoic acid | CHEMBL508378 |
| 22168242 | (2E,4E,6E,10E)-3,7,11,15,19-pentamethylicosa-2,4,6,10,18-pentaenoic acid | |
| 22168239 | (2E,4E,6E)-3,7,11,15-tetramethylhexadeca-2,4,6-trienoic acid | |
| 22168234 | (2E,4E,6E)-3,7,11,15-tetramethylhexadeca-2,4,6,14-tetraenoic acid | |
| 21764469 | (2E,4E)-3-methyl-5-[(1R)-2,6,6-trimethylcyclohex-2-en-1-yl]penta-2,4-dienoic acid | |
| 21650797 | acetyl (2E,4E,6E,8E)-3,7-dimethyl-9-(2,6,6-trimethylcyclohexen-1-yl)nona-2,4,6,8-tetraeneperoxoate | |
| 21525820 | (2E,4E)-7,11,11-trimethyldodeca-2,4-dienoic acid | |
| 21525806 | (2E,4E)-3,7-dimethyldodeca-2,4-dienoic acid | |
| 21291068 | (E)-3,4,4-trimethylhexadec-2-enoic acid | |
| 21291063 | (E)-3,4,4-trimethyltetradec-2-enoic acid | |
| 21291060 | (E)-3,4,4-trimethylpentadec-2-enoic acid | |
| 21291047 | (E)-3,4,4-trimethylheptadec-2-enoic acid | |
| 21291045 | (E)-3,4,4-trimethyloctadec-2-enoic acid | |
| 20830940 | (2E,4E,6Z,8E)-3,7-dimethyl-9-(2,5,6,6-tetramethylcyclohexen-1-yl)nona-2,4,6,8-tetraenoate | |
| 20306860 | (2E,4E)-3,7,11-trimethyldodeca-2,4,11-trienoic acid | |
| 20027300 | azanium (2E,4E,6E,8E)-3,7-dimethyl-9-(2,6,6-trimethylcyclohexen-1-yl)nona-2,4,6,8-tetraenoate | |
| 19609235 | (2E,4E)-2-iodo-3-methyl-5-(2,6,6-trimethylcyclohexen-1-yl)penta-2,4-dienoic acid | |
| 19606927 | (2E,4E,6E,8E)-3,7-dimethyl-9-(2,6,6-trimethyl-4-oxocyclohexen-1-yl)nona-2,4,6,8-tetraenoic acid | |
| 18977382 | (2E,4E,6E,8E)-3,7-dimethyl-9-(2,5,6,6-tetramethylcyclohexen-1-yl)nona-2,4,6,8-tetraenoate | |
| 16061319 | (2Z,4E,6Z,8E)-7-(hydroxymethyl)-3-methyl-9-(2,6,6-trimethylcyclohexen-1-yl)nona-2,4,6,8-tetraenoic acid | 19-Hydroxy-13-cis-retinoic acid; LMPR01090029 |
| 16061318 | (2E,4E,6Z,8E)-7-(hydroxymethyl)-3-methyl-9-(2,6,6-trimethylcyclohexen-1-yl)nona-2,4,6,8-tetraenoic acid | 19-Hydroxy-all-trans-retinoic acid; LMPR01090028 |
| 15125888 | (2E,4E,6E,8E)-2-ethyl-3,7-dimethyl-9-(2,6,6-trimethylcyclohexen-1-yl)nona-2,4,6,8-tetraenoic acid | CHEMBL154239 |
| 11747707 | (2E,4E,6Z,8E)-3,7-dimethyl-9-(6-methylcyclohexen-1-yl)nona-2,4,6,8-tetraenoic acid | |
| 11602784 | (2E,4E)-3-methyl-5-[2-[2-(2,6,6-trimethylcyclohexen-1-yl)ethynyl]cyclohepten-1-yl]penta-2,4-dienoic acid | |
| 10516342 | (2E,4E,6E,8E)-3,7-dimethyl-9-(6-methylcyclohexen-1-yl)nona-2,4,6,8-tetraenoic acid | |
| 10354668 | (Z,4E)-4-(3-ethyl-2-propan-2-ylcyclohex-2-en-1-ylidene)-3-methylbut-2-enoic acid | |
| 10053647 | (2Z,4Z,6E,8E,10E,12E,14E,16E,18E,20E,22E,24E)-2,6,10,14,19,23-hexamethyl-25-(2,6,6-trimethylcyclohexen-1-yl)pentacosa-2,4,6,8,10,12,14,16,18,20,22,24-dodecaenoic acid | |
| 9995780 | (2Z,4E,6E,8E)-3,7-dimethyl-9-(2,6,6-trimethyl-5-oxocyclohexen-1-yl)nona-2,4,6,8-tetraenoic acid | Oxo-13-cis-retinoate; 4-keto-13-cis-retinoate |
| 9949957 | (2E,4E,6E,8E)-3,7-dimethyl-8-[3-(2-methylpropyl)-2-propan-2-ylcyclohex-2-en-1-ylidene]octa-2,4,6-trienoic acid | |
| 9948768 | (2E,4E,6Z,8E)-3,7-dimethyl-9-(2,6,6-trimethyl-5-oxocyclohexen-1-yl)nona-2,4,6,8-tetraenoic acid | |
| 9829386 | (2E,4Z,6E,8E,10E,12E,14E,16E,18E,20E,22E,24E)-2,6,10,14,19,23-hexamethyl-25-(2,6,6-trimethylcyclohexen-1-yl)pentacosa-2,4,6,8,10,12,14,16,18,20,22,24-dodecaenoic acid | |
| 6477090 | (2Z,4Z,6Z,8E,10Z,12Z,14E,16Z,18Z,20E,22Z,24E)-2,6,10,14,19,23-hexamethyl-25-(2,6,6-trimethylcyclohexen-1-yl)pentacosa-2,4,6,8,10,12,14,16,18,20,22,24-dodecaenoic acid | AC1O53P5; 3',4'-Didehydro-,.psi.-caroten-16'-oic acid |
| 6439734 | (2Z,4E,6Z,8E)-3,7-dimethyl-9-(2,2,6-trimethylcyclohexyl)nona-2,4,6,8-tetraenoic acid | 7,8-Dihydroretinoic acid |
| 6437018 | (2Z,4E)-3,7,11-trimethyldodeca-2,4-dienoic acid | AC1O5MUO; EINECS 258-354-9 |

TABLE 1-continued

List of compounds structurally similar to retinoic acid

| CID | IUPAC | Other names |
|---|---|---|
| 6437016 | (2E,4E)-3,7,11-trimethyldodeca-2,4-dienoic acid | AC1O5MUI; CHEMBL37590 |
| 5476505 | (2E,4E)-3-methyl-5-(2,6,6-trimethylcyclohex-2-en-1-yl)penta-2,4-dienoic acid | AC1O5MUI; CHEMBL37590 |
| 5460164 | (2E,4E,6E,8E)-3,7-dimethyl-9-(2,2,6-trimethylcyclohexyl)nona-2,4,6,8-tetraenoic acid | Retinyl ester; all-trans-Retinyl ester |
| 5281248 | (2E,4E,6E,8E,10E,12E,14E,16E,18E,20E,22E,24E)-2,6,10,14,19,23-hexamethyl-25-(2,6,6-trimethylcyclohexanoic acid | NSC635690; Torularhodin; AC1NQY9 |
| 637039 | 2E,4E,6E,8E,10E,12E,14E,16E,18E,20E)-2,6,10,15,19-pentamethyl-21-(2,6,6-trimethylcyclohexen-1-yl)hexanoic acid | Neurosporaxanthin; all-trans-Neurosporaxanthin |
| 428485 | 3-methyl-5-(2,6,6-trimethylcyclohex-2-en-1-yl)penta-2,4-dienoic acid | AC1L8LML; 3-methyl-5-(2,6,6-trimethylcyclohex-2-en-1-yl)penta-2,4-dienoic acid |
| 103723 | 3,7,11-trimethyldodeca-2,4-dienoic acid | |
| 94165 | 2,6,10,14,19,23-hexamethyl-25-(2,6,6-trimethylcyclohexen-1-yl)pentacosa-2,4,6,8,10,12,14,16,18,20,22,24-dodecanenoic acid | AC1L3RN8; NCI60_011910 |
| 56661049 | (2E,4E,6Z,8E)-3,7-dimethyl-9-(4,4,6,6-tetramethyl-2-bicyclo[3.1.1]hept-2-enyl)nona-2,4,6,8-tetraenoic acid | CHEMBL455992 |
| 54581147 | (2E,4E,6Z,8E)-9-[(1S,5R)-6,6-dimethyl-4-bicyclo[3.1.1]hept-3-enyl]-3,7-dimethylnona-2,4,6,8-tetraenoic acid | CHEMBL1773359 |
| 54478024 | 3,4,4-trimethylnon-2-enoic acid | |
| 54476971 | 3,4,4-trimethylundec-2-enoic acid | |
| 54287870 | 3-formyl-7-methyl-9-(2,6,6-trimethylcyclohexen-1-yl)nona-2,4,6,8-tetraenoic acid | RVKZSGIKOAAYJJ-UHFFFAOYSA-N; 293564D2B64FAC5 F524A1B691CBF7C 6B |
| 54116397 | 3,7-dimethyl-2-propan-2-yl-9-(2,6,6-trimethylcyclohexen-1-yl)nona-2,4,6,8-tetraenoic acid | NKQIYDSGIYJXSA-UHFFFAOYSA-N; 5597749F477D668D 55E163C44DA1F3EB |
| 54073647 | 3,4,4-trimethyldec-2-enoic acid | |
| 53995964 | 3-methyl-5-[2-[2-(2,6,6-trimethylcyclohexen-1-yl)ethenyl]cyclohexyl]penta-2,4-dienoic acid | |
| 53919798 | 3,4,4-trimethyldodec-2-enoic acid | |
| 53889922 | 3,7-dimethyl-9-(2,4,4,6,6-pentamethyl-3-oxocyclohexen-1-yl)nona-2,4,6,8-tetraenoic acid | |
| 53887460 | 4-(hydroxymethyl)-3,7-dimethyl-9-(2,6,6-trimethylcyclohexen-1-yl)nona-2,4,6,8-tetraenoic acid | |
| 53854796 | 3-methyl-6-(3,3,7,7-tetramethyl-3a,4,5,6-tetrahydroinden-2-ylidene)hexa-2,4-dienoic acid | |
| 53754609 | 2-ethyl-5,9-dimethyl-11-(2,6,6-trimethylcyclohexen-1-yl)undeca-2,4,6,8,10-pentaenoic acid | |
| 50925583 | (2E,4E,6E,8E)-9-[(1R,2R,4aS,8aR)-1,6-dimethyl-2-propyl-4a,5,8,8a-tetrahydro-2H-naphthalen-1-yl]-8-methylnona-2,4,6,8-tetraenoic acid | |
| 45039634 | (2E,4E,6E,8E)-9-[6,6-dimethyl-3-oxo-2-(trideuteriomethyl)cyclohexen-1-yl]-3,7-dimethylnona-2,4,6,8-tetraenoic acid | |
| 21291081 | (E)-3,4,4-trimethyldec-2-enoic acid | |
| 21291044 | (E)-3,4,4-trimethyldodec-2-enoic acid | |
| 21291042 | (E)-3,4,4-trimethylnon-2-enoic acid | |
| 21291032 | (E)-3,4,4-trimethylundec-2-enoic acid | |
| 19384872 | (E)-4-[(2E,4E,6E,8E)-3,7-dimethyl-9-(2,6,6-trimethylcyclohexen-1-yl)nona-2,4,6,8-tetraenoyl]oxy-4-oxobut-2-enoic acid | |
| 16061321 | (2Z,4E,6Z,8E)-7-formyl-3-methyl-9-(2,6,6-trimethylcyclohexen-1-yl)nona-2,4,6,8-tetraenoic acid | 19-Oxo-9-cis-retinoic acid; LMPR01090031 |
| 16061320 | (2E,4E,6Z,8E)-7-formyl-3-methyl-9-(2,6,6-trimethylcyclohexen-1-yl)nona-2,4,6,8-tetraenoic acid | 19-Oxo-all-trans-retinoic acid; LMPR01090030 |
| 15125894 | (2E,4E,6E,8E)-3,7-dimethyl-2-propan-2-yl-9-(2,6,6-trimethylcyclohexen-1-yl)nona-2,4,6,8-tetraenoic acid | CHEMBL153894 |
| 10043037 | (2E,4E,6E,8E)-3,7-dimethyl-9-(2,4,4,6,6-pentamethyl-3-oxocyclohexen-1-yl)nona-2,4,6,8-tetraenoic acid | CHEMBL103068 |
| 9972939 | (2E,4E,6Z,8E)-3,7-dimethyl-9-(2,6,6-trimethyl-3-oxocyclohexen-1-yl)nona-2,4,6,8-tetraenoic acid | |
| 9906064 | (2E,4E)-3-methyl-5-[(1R)-2-[(E)-2-(2,6,6-trimethylcyclohexen-1-yl)ethenyl]cyclohexyl]penta-2,4-dienoic acid | |
| 9902057 | (2Z,4E,6Z,8E)-4-(hydroxymethyl)-3,7-dimethyl-9-(2,6,6-trimethylcyclohexen-1-yl)nona-2,4,6,8-tetraenoic acid | |

TABLE 1-continued

List of compounds structurally similar to retinoic acid

| CID | IUPAC | Other names |
|---|---|---|
| 6437087 | (2Z,4E,6E,8E)-3,7-dimethyl-9-(2,6,6-trimethyl-3-oxocyclohexen-1-yl)nona-2,4,6,8-tetraenoic acid | Oxoretinoic acid; 4-Oxo-isotretinoin |
| 6437063 | (2E,4E,6E,8E)-3,7-dimethyl-9-(2,6,6-trimethyl-3-oxocyclohexen-1-yl)nona-2,4,6,8-tetraenoic acid | 4-Oxoretinoic acid; 4-Ketoretinoic acid |
| 447276 | (2E,4E,6E,8E)-3,7-dimethyl-9-(2,6,6-trimethylcyclohexa-1,3-dien-1-yl)nona-2,4,6,8-tetraenoic acid | Vitamin A2 acid; 3,4-Didehydroretinoic acid |
| 104857 | 3,7-dimethyl-9-(2,6,6-trimethyl-3-oxocyclohexen-1-yl)nona-2,4,6,8-tetraenoic acid | |

The term "aryl," as used herein, represents a mono- or bicyclic $C_6$-$C_{14}$ group with [4n+2]π electrons in conjugation and where n is 1, 2, or 3. Aryl groups also include ring systems where the ring system having [4n+2]π it electrons is fused to a non-aromatic cycloalkyl or a non-aromatic heterocyclyl. Phenyl is an aryl group where n is 1. Aryl groups may be unsubstituted or substituted with, e.g., 1, 2, 3, or 4 substituent groups as defined herein. Still other exemplary aryl groups include, but are not limited to, naphthyl, 1,2-dihydronaphthyl, 1,2,3,4-tetrahydronaphthyl, fluorenyl, indanyl, and indenyl.

The term "cycloalkyl," as used herein, represents a monovalent saturated or unsaturated non-aromatic cyclic hydrocarbon group from three to ten carbons, unless otherwise specified, and is exemplified by cyclopropyl, cyclobutyl, cyclopentyl, cyclohexyl, cycloheptyl, bicyclo[2.2.1.]heptyl, and the like. In some embodiments, the cycloalkyl is a polycyclic (e.g., adamantyl). Cycloalkyl groups may be unsubstituted or substituted with, e.g., 1, 2, 3, or 4 substituent groups as defined herein.

The term "heteroaryl," as used herein, represents an aromatic (i.e., containing 4n+2 pi electrons within the ring system) 5- or 6-membered ring containing one, two, three, or four heteroatoms independently selected from the group consisting of nitrogen, oxygen, and sulfur, as well as bicyclic, tricyclic, and tetracyclic groups in which any of the aromatic ring is fused to one, two, or three heterocyclic or carbocyclic rings (e.g., an aryl ring). Exemplary heteroaryls include, but are not limited to, furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, isoxazole, isothiazole, pyrazole, thiazole, triazole (e.g., 1,2,4-triazole or 1,2,3-triazole), pyridine, pyrimidine, pyrazine, pyrazine, triazine (e.g., 1,2,3-triazine 1,2,4-triazine, or 1,3,5-triazine), 1,2,4,5-tetrazine, indolyl, quinolinyl, isoquinolinyl, benzimidazolyl, benzothiazolyl, and benzoxazolyl. Heteroaryls may be unsubstituted or substituted with, e.g., 1, 2, 3, or 4 substituents groups as defined herein.

The term "heterocyclyl," as used herein represents a non-aromatic 5-, 6- or 7-membered ring, unless otherwise specified, containing one, two, three, or four heteroatoms independently selected from the group consisting of nitrogen, oxygen, and sulfur. Heterocyclyl groups may be unsubstituted or substituted with, e.g., 1, 2, 3, or 4 substituent groups as defined herein.

Where a group is substituted, the group may be substituted with 1, 2, 3, 4, 5, or 6 substituent groups. Optional substituent groups include, but are not limited to: $C_{1-6}$ alkyl, $C_{2-6}$ alkenyl, $C_{2-6}$ alkynyl, aryl, heteroaryl, cycloalkyl, heterocyclyl, halogen (—F, —Cl, —Br, or —I), azido(—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2H$), carboxylic ester (—$CO_2R'$), carbamoyl (—OC(=O)NR'R" or —NRC(=O)OR'), hydroxy (—OH), oxo (=O), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, aryl, or heteroaryl. In some embodiments, the substituent groups themselves may be further substituted with, for example, 1, 2, 3, 4, 5, or 6 substituents as defined herein. For example, a $C_{1-6}$ alkyl, aryl, or heteroaryl group may be further substituted with 1, 2, 3, 4, 5, or 6 substituents as described herein.

The retinoic acid compounds of the invention inhibit Pin1 activity (e.g., as determined by the fluorescence polarization-based displacement assay or PPIase assay as describe herein). This inhibition can be, e.g., greater than 20%, 30%, 40%, 50%, 60%, 70%, 80%, 90%, 95%, 99%, or greater.

The language "anti-proliferative compound" is intended to include chemical reagents which inhibit the growth of proliferating cells or tissues wherein the growth of such cells or tissues is undesirable. Chemotherapeutic agents are well known in the art (as well as described herein), and are typically used to treat neoplastic diseases, tumors, and cancers.

"Treatment," as used herein, is defined as the application or administration of a therapeutic agent (e.g., a retinoic acid compound) to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease, or to slow the progression of the disease.

As used herein, the terms "sample" and "biological sample" include samples obtained from a mammal or a subject containing Pin1 which can be used within the methods described herein, e.g., tissues, cells and biological fluids isolated from a subject, as well as tissues, cells and fluids present within a subject. Typical samples from a subject include tissue samples, tumor samples, blood, urine, biopsies, lymph, saliva, phlegm, pus, and the like.

By a "low dosage" or "low concentration" is meant at least 5% less (e.g., at least 10%, 20%, 50%, 80%, 90%, or even 95%) than the lowest standard recommended dosage or lowest standard recommended concentration of a particular compound formulated for a given route of administration for treatment of any human disease or condition. For example, a low dosage of an anti-proliferative compound formulated for oral administration will differ from a low dosage of an anti-proliferative compound formulated for intravenous administration.

DETAILED DESCRIPTION OF THE INVENTION

Figure 1A:
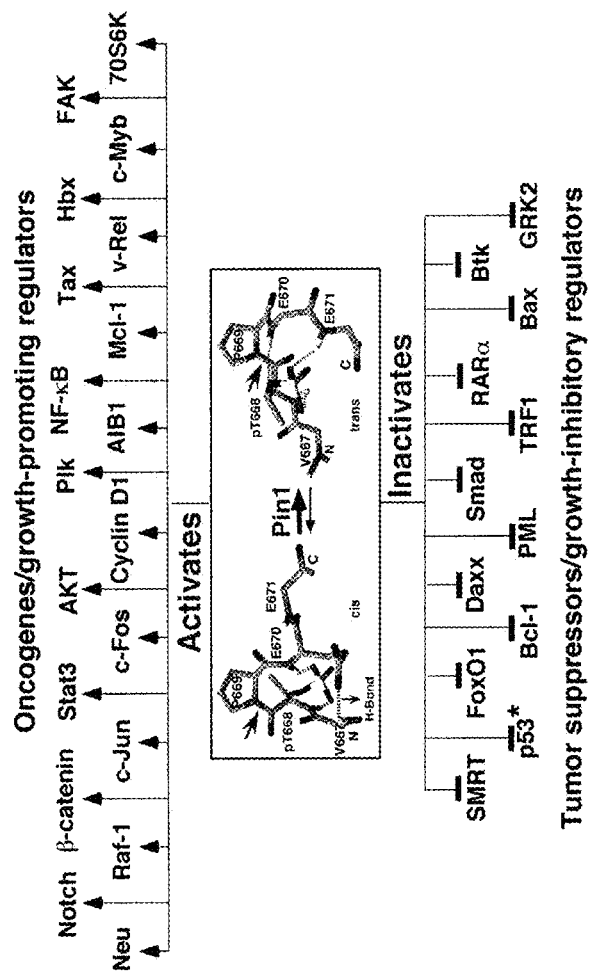
FIG. 1A is a schematic showing relationship between Pin1 and the activity of the indicated genes.
Figure 1B:
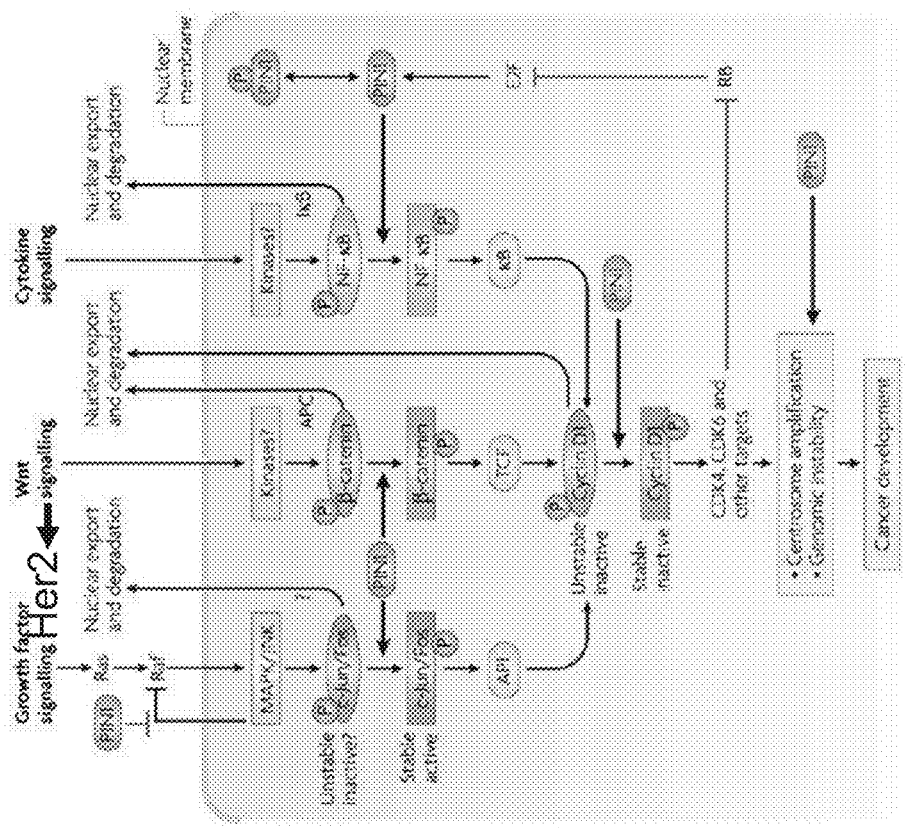
FIG. 1B is a schematic showing the role of Pin1 in the indicated signal transduction pathways.

In general, the invention features methods of treating a proliferative disorder characterized by elevated Pin1 marker levels in a subject by administering a retinoic acid compound. Additionally, the invention features methods of treating proliferative disorders (e.g., proliferative disorders characterized by elevated Pin1 marker levels) by administering a retinoic acid compound in combination with one or more additional anti-proliferative compounds or other anti-cancer therapies.

Inhibitors of Pin1 (e.g., retinoic acid compounds) are useful for treating proliferative disorders (e.g., disorders characterized by increased Pin1 activity). Furthermore, because Pin1 acts in several different oncogenic pathways, Pin1 inhibition would be expected to behave synergistically with many anti-proliferative compounds.

I. Pin1

Phosphorylation on serine/threonine-proline motifs restrains cis/trans prolyl isomerization, and also creates a binding site for the essential protein Pin1. Pin1 binds and regulates the activity of a defined subset of phosphoproteins, as well as participating in the timing of mitotic progression. Both structural and functional analyses have indicated that Pin1 contains a phosphoserine/threonine-binding module that binds phosphoproteins, and a catalytic activity that specifically isomerizes the phosphorylated phosphoserine/threonine-proline. Both of these Pin1 activities are essential for Pin1 to carry out its function in vivo.

Pin1 is overexpressed in human cancer samples and the levels of Pin1 are correlated with the aggressiveness of tumors. We have found that a potent anticancer reagent with an unknown mechanism potently and reversibly inhibits Pin1 isomerase activity. Moreover, inhibition of Pin1 by various approaches, including the Pin1 inhibitor, Pin1 antisense polynucleotides, or genetic depletion, kills human and yeast dividing cells by inducing premature mitotic entry and apoptosis. Thus, upon phosphorylation, Pin1 latches onto phosphoproteins and twists the peptide bond next to the proline, which regulates the function of phosphoproteins and participates in controlling the timing of mitotic progression.

Pin1 is highly conserved and contains a protein-interacting module, called WW domain, and a catalytically active peptidyl-prolyl isomerase (PPIase). Pin1 is structurally and functionally distinct from members of two other well-characterized families of PPIases, the cyclophilins and the FKBPs. PPIases are ubiquitous enzymes that catalyze the typically slow prolyl isomerization of proteins, allowing relaxation of local energetically unfavorable conformational states. Phosphorylation on Ser/Thr residues immediately preceding Pro not only alters the prolyl isomerization rate, but also creates a binding site for the WW domain of Pin1. The WW domain acts a novel phosphoserine-binding module targeting Pin1 to a highly conserved subset of phosphoproteins. Furthermore, Pin1 displays a unique phosphorylation-dependent PPIase that specifically isomerizes phosphorylated Ser/Thr-Pro bonds and regulates the function of phosphoproteins.

Taken together, these results indicate that the Pin1 subfamily of enzymes is a diagnostic and therapeutic target for diseases characterized by uncontrolled cell proliferation, primarily malignancies.

II. Measurement of PIN1 Marker Levels

The present invention pertains to the treatment of proliferative diseases identified as coinciding with elevated Pin1 marker levels with retinoic acid compounds. In some aspects, the invention features the determination of Pin1 marker levels in a subject; where retinoic acid is administered in subjects where Pin1 marker levels are determined to be elevated. In other aspects, the invention can also feature the measurement of Pin1 marker levels subsequent to the administration of retinoic acid compounds in order to evaluate the progress of therapy in treating the proliferative disorder.

Accordingly, one aspect of the present invention relates to diagnostic assays for measuring levels of Pin1 marker, as well as Pin1 activity, in the context of a biological sample (e.g., tumor samples, blood, urine, biopsies, lymph, saliva, phlegm, and pus) to thereby determine whether an individual is a candidate for treatment with a retinoic acid compound. The invention features both treatment of subjects exhibiting symptoms of a proliferative disorder and individuals at risk for developing a proliferative disorder.

Diagnostic Assays

An exemplary method for detecting the presence or absence of Pin1 protein or nucleic acid in a biological sample involves obtaining a biological sample from a test subject and contacting the biological sample with a compound or an agent capable of detecting Pin1 protein or a nucleic acid (e.g., mRNA, genomic DNA) that encodes Pin1 protein such that the presence of Pin1 protein or nucleic acid is detected in the biological sample. A preferred agent for detecting Pin1 mRNA or genomic DNA is a labeled nucleic acid probe capable of hybridizing to Pin1 mRNA or DNA. The nucleic acid probe can be, for example, a Pin1 nucleic acid or a corresponding nucleic acid such as an oligonucleotide of at least 15, 30, 50, 100, 250 or 500 nucleotides in length which is capable of specifically hybridizing under stringent conditions to Pin1 mRNA or genomic DNA. Other suitable probes for use in the diagnostic assays of the invention are described herein.

A preferred agent for detecting Pin1 marker is an antibody capable of binding to Pin1 protein, preferably an antibody with a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

With respect to antibody-based detection techniques, one of skill in the art can raise anti-Pin1 antibodies against an appropriate immunogen, such as isolated and/or recombinant Pin1 or a portion or fragment thereof (including synthetic molecules, such as synthetic peptides) using no more than routine experimentation. Synthetic peptides can be designed and used to immunize animals, such as rabbits and mice, for antibody production. The nucleic and amino acid sequence of Pin1 is known (Hunter et al., WO 97/17986 (1997); Hunter et al., U.S. Pat. Nos. 5,952,467 and 5,972,697, the teachings of all of which are hereby incorporated by reference in their entirety) and can be used to design nucleic acid constructs for producing proteins for immunization or in nucleic acid detection methods or for the synthesis of peptides for immunization.

Conditions for incubating an antibody with a test sample can vary depending upon the tissue or cellular type. Incubation conditions can depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques," Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of enzyme Immunoassays: Laboratory Techniques in Biochemistry and Molecular Biology," is Elsevier Science Publishers, Amsterdam, The Netherlands (1985).

The detection method of the invention can be used to detect Pin1 mRNA, protein, or genomic DNA in a biological sample in vitro as well as in vivo. For example, in vitro techniques for detection of Pin1 mRNA include Northern hybridizations and in situ hybridizations. In vitro techniques for detection of Pin1 protein include enzyme linked immunosorbent assays (ELISAs), Western blots, immunoprecipitations, immunofluorescence, or quantitative sequencing reactions. In vitro techniques for detection of Pin1 genomic DNA include Southern hybridizations. The detection of genomic mutations in Pin1 (or other genes that effect Pin1 marker levels) can be used to identify inherited or somatic mutations. Furthermore, in vivo techniques for detection of Pin1 protein include introducing into a subject a labeled anti-Pin1 antibody. For example, the antibody can be labeled with a radioactive marker whose presence and location in a subject can be detected by standard imaging techniques.

In another embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Pin1 marker such that the presence of Pin1 marker is detected in the biological sample, and comparing the presence of Pin1 marker in the control sample with the presence of Pin1 marker in the test sample.

The immunological assay test samples of the present invention may include cells, protein or membrane extracts of cells, blood or biological fluids such as ascites fluid or brain fluid (e.g., cerebrospinal fluid). The test sample used in the above-described method is based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized. The invention also encompasses kits for detecting the presence of Pin1 in a biological sample. For example, the kit can comprise a labeled compound or agent capable of detecting Pin1 protein or mRNA in a biological sample; means for determining the amount of Pin1 in the sample; and means for comparing the amount of Pin1 in the sample with a standard. The compound or agent can be packaged in a suitable container. The kit can further comprise instructions for using the kit to detect Pin1 protein or nucleic acid.

Pin1 marker levels can also be measured in an assay designed to evaluate a panel of target genes, e.g., a microarray or multiplex sequencing reaction. In the embodiments of the invention described herein, well known biomolecular methods such as northern blot analysis, RNase protection assays, southern blot analysis, western blot analysis, in situ hybridization, immunocytochemical procedures of tissue sections or cellular spreads, and nucleic acid amplification reactions (e.g., polymerase chain reactions) may be used interchangeably. One of skill in the art would be capable of performing these well-established protocols for the methods of the invention. (See, for example, Ausubel, et al., "Current Protocols in Molecular Biology," John Wiley & Sons, NY, N.Y. (1999)).

Diagnostic assays can be carried out in, e.g., subjects diagnosed or at risk of a proliferative disorder. Such disorders include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

Prognostic Assays

The diagnostic methods described herein can furthermore be utilized to identify subjects having or at risk of developing a disease or disorder associated with aberrant Pin1 expression or activity. For example, the assays described herein, such as the preceding diagnostic assays or the following assays, can be utilized to identify a subject having or at risk of developing a disorder associated with Pin1 marker (e.g., a proliferative disorder). Thus, the present invention provides a method for identifying a disease or disorder associated with aberrant Pin1 expression or activity in which a test sample is obtained from a subject and Pin1 protein or nucleic acid (e.g., mRNA, genomic DNA) is detected, wherein the presence of Pin1 protein or nucleic acid is diagnostic for a subject having or at risk of developing a Pin1-associated disorder and are, therefore, susceptible to treatment with a retinoic acid compound.

Furthermore, the present invention provides methods for determining whether a subject can be effectively treated with a retinoic acid compound for a disorder associated with aberrant Pin1 expression or activity in which a test sample is obtained and Pin1 protein or nucleic acid expression or activity is detected (e.g., wherein the abundance of Pin1 protein or nucleic acid expression or activity is diagnostic for a subject that can be administered the agent to treat a disorder Pin1-associated disorder).

In one embodiment, the present invention provides methods for determining Pin1 post-translational modifications. For example, phosphorylation of Pin1 on Ser71 in the catalytic active site by the tumor suppressor DAPK1 completely inhibits Pin1 catalytic activity and cell function to promote oncogenesis. More importantly, phosphorylation of Pin1 on Ser71 in the catalytic active site also prevents retinoic acid compounds from binding to Pin1 active site and induce Pin1 degradation and to inhibit Pin1 function. Therefore, by detecting reduced Ser71 phosphorylation using phospho-specific Pin1 antibodies that we have generated can be a method to select patients for RA treatments and to explain some patients may not respond to RA. Because aberrantly proliferating cells exhibit reduced Ser71 phosphorylation, these cells are more sensitive to RA treatments compared to normal cells.

The methods of the invention can also be used to detect genetic alterations in a Pin1 gene, thereby determining if a subject with the altered gene is at risk for a disorder associated with the Pin1 gene and, consequently, a candidate for retinoic acid therapy. In preferred embodiments, the methods include detecting, in a sample of cells from the subject, the presence or absence of a genetic alteration characterized by at least one of an alteration affecting the integrity of a gene encoding a Pin1-protein, or the misexpression of the Pin1 gene. For example, such genetic alterations can be detected by ascertaining the existence of at least one of 1) a deletion of one or more nucleotides from a Pin1 gene; 2) an addition of one or more nucleotides to a Pin1 gene; 3) a substitution of one or more nucleotides of a Pin1 gene, 4) a chromosomal rearrangement of a Pin1 gene; 5) an alteration in the level of a messenger RNA transcript of a Pin1 gene, 6) aberrant modification of a Pin1 gene, such as of the methylation pattern of the genomic DNA, 7) the presence of a non-wild type splicing pattern of a messenger RNA transcript of a Pin1 gene, 8) a non-wild type level of a Pin1-protein, 9) allelic loss of a Pin1 gene, and 10) inappropriate post-translational modification of a Pin1-protein. As described herein, there are a large number of assay techniques known in the art which can be used for detecting alterations in a Pin1 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the Pin1-gene (see Abravaya et al. (1995) Nucleic Acids Res 0.23:675-682). This method can include the steps of collecting a sample from a patient, isolating nucleic acid (e.g., genomic, mRNA or both) from the sample, contacting the nucleic acid sample with one or more primers which specifically hybridize to a Pin1 gene under conditions such that hybridization and amplification of the Pin1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874-1878), transcriptional amplification system (Kwoh, D. Y. et al, (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Pin1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Pin1 can be identified by hybridizing a sample and control nucleic acids, e.g., DNA or RNA, to high density arrays containing hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in Pin1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Pin1 gene and detect mutations by comparing the sequence of the sample Pin1 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the Pin1 gene include methods in which protection from cleavage agents is used to detect mismatched bases in RNA/RNA or RNA/DNA heteroduplexes (Myers et al. (1985) Science 230: 1242). In general, the art technique of "mismatch cleavage" starts by providing heteroduplexes formed by hybridizing (labeled) RNA or DNA containing the wild-type Pin1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with Si nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Nat Acad Sci USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Pin1 cDNAs obtained from samples of cells. For example, the mutY enzyme of E. coli cleaves A at G/A mismatches and the thymidine DNA glycosylase from HeLa cells cleaves Tat G/T mismatches (Hsu et al. (1994) Carcinogenesis 15:1657-1662). According to an exemplary embodiment, a probe based on a Pin1 sequence, e.g., a wild-type Pin1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Pin1 genes. For example, single strand conformation polymorphism (SSCP) may be used to detect differences in electrophoretic mobility between mutant and wild type nucleic acids (Orita et al. (1989) Proc Natl. Acad. Sci. USA: 86:2766, see also Cotton (1993) Mutat Res 285:125-144; and Hayashi (1992) Genet Anal Tech Appl 9:73-79). Single-stranded DNA fragments of sample and control Pin1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner et al. (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Pin1 gene.

Furthermore, any cell type or tissue in which Pin1 is expressed may be utilized in the prognostic assays described herein.

As with the diagnostic assay described above, prognostic assays of Pin1 activity can be included as part of a panel of target genes.

Additional methods of detecting Pin1 activity and diagnosing Pin1 related disorders are disclosed in U.S. Patent Application Publication Nos.: 2009/0258352, 2008/0214470, 2006/0074222, 2005/0239095, US2002/0025521, U.S. Pat. No. 6,495,376, and PCT Application Publication No. WO02/065091, each of which is hereby incorporated by reference in its entirety.

The present invention also features methods and compositions to diagnose, treat and monitor the progression of a disorder described herein (e.g., a cellular proliferation disorder) by detection and measurement of, for example, Pin1 substrates (or any fragments or derivatives thereof) containing a phosphorylated Ser/Thr-Pro motif in a cis or trans conformation, as described in U.S. Patent Provisional Application No. 61/255,431, which is hereby incorporated by reference in its entirety. The methods can include measurement of absolute levels of the Pin1 substrate (examples of which are listed in Tables 2, 3 and 4) in a cis or trans conformation as compared to a normal reference, using conformation specific antibodies. For example, a serum level or level in a biopsy of a Pin1 substrate in the cis or trans conformation that is less than 5 ng/ml, 4 ng/ml, 3 ng/ml, 2 ng/ml, or less than 1 ng/ml serum or a biopsy is considered to be predictive of a good outcome in a patient diagnosed with a disorder (e.g., a disorder associated with a deregulation of Pin1 activity). A serum level of the substrate in the cis or trans conformation that is greater than 5 ng/ml, 10 ng/ml, 20 ng/ml, 30 ng/ml, 40 ng/ml, or 50 ng/ml is considered diagnostic of a poor outcome in a subject already diagnosed with a disorder, e.g., associated with a deregulation of Pin1 activity.

For diagnoses based on relative levels of substrate in a particular conformation (e.g., a Pin1 substrate in the cis or trans conformation), a subject with a disorder (e.g., a disorder associated with a deregulation of PPIase activity) will show an alteration (e.g., an increase of 10%, 20%, 30%, 40%, 50%, 60%, 70%, 80%, 90%, or more) in the amount of the substrate in, for example, the cis conformation. A normal reference sample can be, for example, a prior sample taken from the same subject prior to the development of the disorder or of symptoms suggestive of the disorder, a sample from a subject not having the disorder, a sample from a subject not having symptoms of the disorder, or a sample of a purified reference polypeptide in a given conformation at a known normal concentration (i.e., not indicative of the disorder).

Standard methods may be used to measure levels of the substrate in any bodily fluid, including, but not limited to, urine, blood, serum, plasma, saliva, amniotic fluid, or cerebrospinal fluid. Such methods include immunoassay, ELISA, Western blotting, and quantitative enzyme immunoassay techniques.

For diagnostic purposes, the conformation-specific antibodies may be labeled. Labeling of the antibody is intended to encompass direct labeling of the antibody by coupling (e.g., physically linking) a detectable substance to the antibody, as well as indirect labeling the antibody by reacting the antibody with another reagent that is directly labeled. For example, the antibody can be labeled with a radioactive or fluorescent marker whose presence and location in a subject can be detected by standard imaging techniques.

The diagnostic methods described herein can be used individually or in combination with any other diagnostic method described herein for a more accurate diagnosis of the presence or severity of a disorder (e.g., a cellular proliferation disorder or a neurological disorder). Examples of additional methods for diagnosing such disorders include, e.g., examining a subject's health history, immunohistochemical staining of tissues, computed tomography (CT) scans, or culture growths.

Monitoring the Effects of Retinoic Acid Treatment, and Disease Progression

In one embodiment, the present invention features a method for monitoring the effectiveness of treatment of a subject with a retinoic acid compound comprising the steps of (i) obtaining a pre-administration sample from a subject prior to administration of the compound; (ii) detecting the level of expression or activity of a Pin1 protein, Pin1 phosphorylation on Ser71, mRNA, or genomic DNA in the pre-administration sample; (iii) obtaining one or more post-administration samples from the subject; (iv) detecting the level of expression or activity of the Pin1 protein, mRNA, or genomic DNA in the post-administration samples; (v) comparing the level of expression or activity of the Pin1 protein, mRNA, or genomic DNA in the pre-administration sample with the Pin1 protein, mRNA, or genomic DNA in the post administration sample or samples; and (vi) altering the administration of the retinoic acid compound to the subject accordingly. According to such an embodiment, Pin1 expression, phosphorylation or activity may be used as an indicator of the effectiveness of the retinoic acid compound, even in the absence of an observable phenotypic response.

In another embodiment, the diagnostic methods described herein can also be used to measure the levels of, for example, polypeptides (e.g., Pin1 substrates listed in Tables 2, 3 and 4) with pSer/Thr-Pro motifs in the cis or trans conformation using conformation specific antibodies, The methods can include repeated measurements, using conformation specific antibodies, for diagnosing the disorder and monitoring the treatment or management of the disorder. In order to monitor the progression of the disorder in a subject, subject samples can be obtained at several time points and conformation specific antibodies can be used to monitor the levels of cis and trans isomers of Pin1 substrates (listed in Tables 2, 3 and 4). For example, the diagnostic methods can be used to monitor subjects during chemotherapy (e.g., therapy with a retinoic acid compound or other agent described herein). In this example, serum samples from a subject can be obtained before treatment with a chemotherapeutic agent, again during treatment with a chemotherapeutic agent, and again after treatment with a chemotherapeutic agent. In this example, the level of Pin1 substrate with a pSer/Thr-Pro motif in the cis conformation in a subject is closely monitored using the conformation-specific antibodies of the invention and, if the level of Pin1 substrate with a pSer/Thr-Pro motif in the cis conformation begins to increase during therapy, the therapeutic regimen for treatment of the disorder can be modified as determined by the clinician (e.g., the dosage of the therapy may be changed or a different therapeutic may be administered). The monitoring methods of the invention may also be used, for example, in assessing the efficacy of a particular drug or therapy in a subject, determining dosages, or in assessing progression, status, or stage of the infection.

TABLE 2

General Pin1 Substrates

| Substrate (GenBank Accession Number) | Targeting Site(s) | Functional Consequence of PPIase Activity of Pin1 Upon Substrate |
|---|---|---|
| G2/M and Mitotic Regulation | | |
| NIMA (P11837) | — | Regulation of mitotic function |
| RAB4 (NP_004569) | — | — |
| CDC25 (AAA58417) | pThr48/67-Pro | Dephosphorylation and regulation of activity |
| WEE1 | pT186-P | Inhibition of WEE1 |

TABLE 2-continued

General Pin1 Substrates

| Substrate (GenBank Accession Number) | Targeting Site(s) | Functional Consequence of PPIase Activity of Pin1 Upon Substrate |
|---|---|---|
| (NP_003381) | | activity |
| PLK1 (P53350) | — | — |
| MYT1 (NP_004194) | — | — |
| CDC27 (AAH11656) | — | — |
| CENP-F (P49454) | — | — |
| Incenp (NP_064623) | — | — |
| RPB1 (CAA65619) | pSer5-Pro | Regulation of CTD dephosphorylation |
| NHERF-1 (AAA80218) | pSer279/301-P | Dephosphorylation |
| KRMP1 (NP_057279) | pT-1604-P | Regulation of mitotic function |
| CK2 (NP_808227) | Multiple pSer/Thr-Pro sites | Inhibition of kinase activity |
| TopoIIα (NP_001058) | — | Inhibition or induction of phosphorylation |
| DAB2 (NP_001334) | — | Dephosphorylation |
| p54nrb (CAA72157) | Multiple pSer/Thr-Pro sites | — |
| Sil (CAC14001) | Multiple pSer/Thr-Pro sites | Regulation of function |
| EMI1 (NP_036309) | pS10-P | Stabilization |
| G1/S Regulation | | |
| Cyclin D1 (NP_444284) | pT286-P | Stabilization and nuclear localization |
| Ki67 | pT234-P | — |
| c-Myc (CAA46984) | pT58-P | Dephosphorylation and destabilization |
| Cyclin E (P24864) | pS384-P | Destabilization |
| Growth and Oncogenic Signaling | | |
| c-Jun (AAH06175) | pS63/73-P | Transactivation |
| B-catenin (P35222) | pS246-P | Stabilization, protein interaction, and transactivation |
| Cf-2 (NP_034298) | — | Destabilization |
| NF-κB (AAH33210) | pT254-P | Stabilization, protein interaction, and transactivation |
| RAF1 (AAA60247) | Multiple pSer/Thr-Pro sites | Dephosphorylation and prolonging activation |
| c-Fos (CAA24756) | Multiple pSer/Thr-Pro sites | Transactivation |
| RARα (NP_001019980) | pS77-P | Stabilization and transactivation |
| AIB1/SRC-3 | — | Transactivation and destabilization |
| HBx (NP_110380) | pS41-P | Stabilization and potentiation |
| STAT3 (NP_998827) | pS727-P | Transactivation |
| DNA Damage, Oxidative Stress Response, and Apoptosis | | |
| p53 (BAC16799) | Multiple pSer/Thr-Pro sites | Stabilization and transactivation |
| Bcl-2 (NP_000648) | pS70/87-P | — |
| p73 (CAA72221) | Multiple pSer/Thr-Pro sites | Stabilization and transactivation |
| BimEL (AAC39593) | pS65-P | Stabilization |

TABLE 2-continued

General Pin1 Substrates

| Substrate (GenBank Accession Number) | Targeting Site(s) | Functional Consequence of PPIase Activity of Pin1 Upon Substrate |
|---|---|---|
| p66$^{Shc}$ (AAH14158) | — | Mitochondrial import |
| CHE1 (P06276) | — | Destabilization |
| *Neuronal Survival and Degeneration* | | |
| Tau (NP_058519) | pT231-P pT212-P | Dephosphorylation and protein interaction |
| APP (P05067) | pT668-P | Promotes non-amyloidogenic APP processing and reduces Aβ production |
| APP fragment | pT668-P | Increases Aβ production from C99 APP fragment |
| Synphilin-1 (AAD30362) | pS211/215-P | Protein interaction |
| Gephyrin (CAC81240) | pS188/194/200-P | Protein interaction |
| MCL1 (CAI15504) | pT163-P | Stabilization |
| *Immune Response and Asthma* | | |
| NFAT (NP_666017) | — | — |
| AUF1 (NP_112738) | — | Protein interaction |
| IRF3 (AAH71721) | pS339-P | Destabilization |
| BTK (CAI42359) | pS21/115-P | Destabilization |
| *Others* | | |
| SIN2-RPD3 | — | Reduces histone deacetylases |
| hSpt5 (NP_001124297) | — | — |

TABLE 3A

Pin1 targets where Pin1 prevents protein from degradation

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 1 | p53 | 1. Stabilization; Increase p53 promoter binding activity  2. Pin1 in formation of HMWC and stabilizes p53 | Ser33, Ser315, Thr181; Pro82 | Chk2 | Genotoxic stress, DNA damage Trophoblast invasiveness |
| 2 | Cyclin D1 | Stabilization; localization and transcription | Thr286 | Block Socs-1 ub-mediated proteolysis | Cell proliferation/ cancers |
| 3 | Tau | 1. Dephosphorylated at Thr231  2. Pin1 knockdown or KO increased WT tau protein stability in vitro | Thr231 | | Tauopathy |
| 4 | β-Catenin | Stability; localization and transactivation | Ser246 | Could stabilize β-catenin by inhibiting GSK-3β dependent degradation | Cell proliferation/cancers |
| 5 | c-Jun | Transcriptional activity | Ser63/Ser73 | JNK | Breast cancer; AML |
| 6 | p65/NF-kB | Nuclear translocation; stability | Thr254 | | Cytokines; Hepatocyte NF-kappaB activation |
| 7 | p73 | Stabilizing, transcriptional activity | Ser412, Thr442 and Thr482 | c-Abl and p300 | Genotoxic stress |
| 8 | Synphilin-1 | Facilitates Lewy Body formation; stabilizes alpha-synuclein | Ser211 and Ser215 | casein kinase II | Parkinson disease |
| 9 | c-Fos | Transcriptional activation | C-terminal | ERK | |
| 10 | Sil | No impact on Sil spindle checkpoint | | | Unknown |
| 11 | p54nrb | | Thr412, Thr430 and Thr452 | Cdk1 | |
| 12 | Bruton tyrosine kinase (Btk) | Mediates Btk degradation | Ser21 an Ser115 | | Tyrosine kinase |
| 13 | AUF1 | Regulates GM-CSF mRNA; AUF1, AU rich element-binding protein | Ser83 | | |
| 14 | BIM$_{EL}$ | Stabilize BIM$_{EL}$ and induce apoptosis | Ser65 | JIP3, MKK7 and JNK | Neuronal apoptosis |

TABLE 3A-continued

Pin1 targets where Pin1 prevents protein from degradation

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 15 | Mcl-1 (Myeloid cell leukemia sequence-1) | 1. Pin1 inhibits Mcl-1 ubiquitination<br>2. Stabilizes Mcl-1 | Thr163; Thr92 | JNK3 induces Mcl-1 degradation by counting the protective binding of Pin1 Erk phosphorylates Thr92 and Thr163 | Oligodendrocyte apoptosis; Mcl-1 mediated chemoresistance; breast cancer |
| 16 | HBx; Hepatitis B virus encoded protein X | Pin1 overexpression increased the protein stability of HBx | Ser41 | Pin1 binds HBx and enhance hepatocarcinogenesis in HBV-infected hepatocytes | Hepatocarcinogenesis |
| 17 | Origin recognition complex, subunit 1 (ORC1) | Prevents degradation of ORC1 by inactivating mitotic APC complex | | APC; Topo II | Mitotisis; chromosome segregation and for reprogramming replicons |
| 18 | Bcl-2 | 1. Induce changes in the bioactivity of Bcl-2;<br>2. Prevents dephosphorylation of Bcl-2 | | Possibly mediated by cdc2 | |
| 19 | Erb2 | Stabilize ErbB2 | Ubiquitinated erbB2 | ErbB2 pathway; ubiquitin mediated degradation | Her2-positive breast cancer |
| 20 | PPARγ | Prevents the polyubiquitination of PPARγ through ubiquitin-proteosome pathway | Ser84 | Ras mediated kinase | Macrophages mediated atherosclerosis |
| 21 | Cep55 | Increased Cep55 stability | Ser425, Ser428 | Cdk1, Plk1 | Mitosis and cytokinesis |
| 22 | Spt23 | Ess1 stabilizes Spt23 | Ser654 | | Unsaturated fatty-acid synthesis |
| 23 | p27 | Pin1 protects p27 from degradation through polyubiquitination mechanism. | Thr187 | Cdk2 | Cell cycle; Cancer |
| 24 | Akt | Regulates Akt protein stability | Thr92, Thr450 | | Oncogenesis |
| 25 | HTLV Tax protein | Increased Tax protein expression; inhibits Tax protein degradation | Ser160 | | Pathogenesis of Human T-cell leukemia virus type 1 (HTLV-1) related diseases |
| 26 | Nanog | Leads to Nanog stability | Ser52, Ser65 | | Stem cells pluripotency; cell renewal |
| 27 | Viral Integrase | Stabilized phospho-HIV-1 integrase | Ser57 | JNK | HIV-1 cDNA integration and infection |

TABLE 3B

Pin1 targets where Pin1 enhances degradation of phosphorylated proteins

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 1 | c-Myc | Enhances c-Myc degradation | Thr58 | | Tumorgenesis |
| 2 | Cyclin E | Depletion of Pin1 upregulates cellular level of cyclin E | Ser384 | Cyclin E-Cdk2 complex | Cell cycle, genomic instability and tumorigenesis |
| 3 | SRC-3/AIB1 | Enhances SRC-3 degradation | N/A | Steroid receptor | |
| 4 | RARα | Induces its degradation | Ser77 | | Retinoic acid receptor; |
| 5 | IRF3 | Promote its degradation via the ubiquitin-proteasome pathway. | Ser339 | | Host antiviral responses during virus infection |

TABLE 3B-continued

Pin1 targets where Pin1 enhances degradation of phosphorylated proteins

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 6 | Che-1 | Conformational changes induced by Pin1 are requested for Che-1/HDM2 interaction | Thr144 | | p53 transcription; DNA damage apoptotic pathway |
| 7 | Pim-1 protein kinase | Binding of Pin1 leads to a decrease in the protein level of Pim-1 | N/A | PP2A | Elevated in lymphomas leukemias and prostate cancer through c-Myc pathway |
| 8 | Promyelocytic leukemia protein (PML) | Binds to phosphorylated C terminus of PML and enhances PML degradation | C-terminal of PML (Ser403, Ser505, Ser518 and Ser527) | | Breast cancer; hydrogen peroxide-induced death; cell proliferation |
| 9 | FOXO | A novel negative FOXO regulator, interconnecting FOXO phosphorylation and monoubiquitination in response to cellular stress to regulate p27 | | | Oxidative stress |
| 10 | Silencing mediator for retinoic acid and thyroid hormone receptor (SMRT) | Pin1 destabilizes SMRT | Ser1241, Thr1445, Ser1469 | Her2/Neu/ErbB2 receptor; Cdk2 | Human cancer |
| 11 | TRF-1 | Pin1 inhibition resulted in decrease TRF1 degradation; | Thr149 | Cdk | Cancer; ageing |
| 12 | G protein-coupled receptor kinase 2 (GRK2) | Promotes GRK2 degradation | Ser670 | CDK2-cyclinA | Cell cycle progression; p53 response and the induction of apoptosis |
| 13 | SF-1 | Pin1 promotes SF-1 ubiquitination and degradation | Ser203 | CDK7 | Gonadotropin beta-subunit gene transcription |
| 14 | Sulfotransferase 4A1 (SULT4A1) | Pin1 destabilizes SULT4A1 | Thr8, Thr11 | ERK1 and PP2A | Metabolism of endogenous and exogenous compounds |
| 15 | Smad2/ Smad3 | Reduced Smad2/3 protein levels | Thr179, Ser204, Ser208, Ser213 (Smad3 linker domain) | Smurf2 with Smads and enhanced Smad ubiquitination | TGF-β signaling |
| 16 | MEF2C | Pin1 decreases MEF2C stability | Ser98/Ser110 | | Muscle terminal differentiation |

TABLE 3C

Pin1 targets where Pin1 regulates target phosphorylation/dephosphorylation/other modifications

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 1 | Tau | Enhance dephosphorylation at Thr231 | Thr231 | | Neuronal differentiation; stress induced; Alzheimer disease |
| 2 | Raf-1 | Dephosphorylation by PP2A | N.A. | Ras/MAP Kinase | |
| 3 | Type-1 protein phosphatase Inhibitor-2 (I-2) | Cycling phosphorylation in mitotic | Thr72 | CDK1-cyclin B | Entry and exit in mitotic |
| 4 | TGF-β1 mRNA | Decay, accumulation and translation of TGF-β1 mRNA in Eosinophils | | | Chronic asthma |

TABLE 3C-continued

Pin1 targets where Pin1 regulates target phosphorylation/dephosphorylation/other modifications

| PROTEIN NAME | PIN1 FUNCTION | PIN1 BINDING MOTIF | KINASE/ PHOSPHATASE | PATHWAYS/ DISEASES/ MECHANISM |
|---|---|---|---|---|
| 5 K-homology splicing regulator protein (KSRP) | parathyroid hormone (PTH) mRNA stability | Ser181 | | |

TABLE 4

Pin1-targets for promoting tumorigenesis

| Substrates | Function | Binding Sites | Effects | Activation/ Inactivation |
|---|---|---|---|---|
| AIB1/SRC3 | Transactivator | — | Activity | + |
| Akt | Protein kinase | pThr$^{92/450}$-Pro | Stability | + |
| Bax | Apoptosis | pThr$^{167}$-Pro | Activity | − |
| Bcl-2 | Antiapoptic protein | — | Stability | − |
| Btk | Tyrosine kinase | pSer$^{21/115}$-Pro | Stability | − |
| β-catenin | Transcription factor | pSer$^{246}$-Pro | Localization, stability | + |
| C/EBP | Transcription factor | — | Activity | − |
| Cyclin D1 | Transcription factor | pThr$^{286}$-Pro | Localization, stability | + |
| Daxx | Apoptosis | pSer$^{178}$-Pro | Stability | − |
| FAK | Tyrosine kinase | pSer$^{910}$-Pro | Activity | + |
| c-Fos | Transcription factor | — | Activity | + |
| FOXO4 | Transcription factor | — | Localization, activity | − |
| GRK2 | G protein receptor | pSer$^{670}$-Pro | Stability | − |
| Hbx | Transactivator | pSer$^{41}$-Pro | Activity, stability | + |
| c-Jun | Transcription factor | pSer$^{63/73}$-Pro | Activity, stability | + |
| Mcl-1 | Apoptosis | pThr$^{92/163}$-Pro | Stability | + |
| c-Myb | Transactivator | pSer$^{528}$-Pro | Activity | + |
| Neu | Growth factor receptor | — | Stability | + |
| NF-κB | Transcription factor | pThr$^{254}$-Pro | Localization, stability | + |
| Notch1 | Growth factor | — | Activity | + |
| p70S6K | Ribosomal S6 kinases | — | Activity | + |
| p53 | Transcription factor | — | Activity, stability | −* |
| Plk1 | Mitotic kinase | — | Binding activity | + |
| PML | Transcription factor | pSer$^{403/505/518/527}$-Pro | Stability | − |
| Raf-1 | Protein kinase | — | Activity | + |
| RARα | Transcriptional regulator | pSer$^{77}$-Pro | Stability | − |
| V-Rel | Transcription factor | pThr$^{254}$-Pro | Localization, stability | + |
| Smad | Transactivator | — | Stability | − |
| SMRT | Transcriptional co-repressor | pSer$^{1241/1469}$, Thr$^{1445}$-Pro | Stability | − |
| Stat3 | Transcription factor | pSer$^{727}$-Pro | Activity | + |
| Tax | Viral oncoprotein | pSer$^{160}$-Pro | Activity, stability | + |
| Pin2/TRF1 | Telomere regulation | pThr$^{149}$-Pro | Stability | − |

III. Methods of Treatment

The present invention provides for both prophylactic and therapeutic methods of treating a subject at risk of (or susceptible to) a proliferative disorder (e.g., a disorder associated with increased Pin1 expression or activity) with a retinoic compound.

Certain embodiments of the invention feature formulation of a retinoic acid compound for, e.g., controlled or extended release. Many strategies can be pursued to obtain controlled and/or extended release in which the rate of release outweighs the rate of metabolism of the therapeutic compound. For example, controlled release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes. The release mechanism can be controlled such that the retinoic acid compound is released at period intervals, the release could be simultaneous, or a delayed release of one of the agents of the combination can be affected, when the early release of one particular agent is preferred over the other.

Certain embodiments of the invention feature a deuterated retinoic acid compound that is made by replacing some or all hydrogen with deuterium using state of the art techniques (e.g., as described herein and at www.concertpharma.com).

Prophylactic Methods

In one aspect, the invention provides a method for preventing a proliferative disorder in a subject by administering to the subject a retinoic acid compound. Subjects at risk for a disease which is caused or contributed to by aberrant Pin1 expression or activity can be identified by, for example, any or a combination of diagnostic or prognostic assays as described herein. Administration of a retinoic acid compound can occur prior to the manifestation of symptoms characteristic of the Pin1 aberrancy, such that a disease or disorder is prevented or, alternatively, delayed in its progression.

Combination Therapies

Anti-proliferative and other anti-cancer compounds (e.g., anti-angiogenic compounds) are useful for treating proliferative disorders in combination with the retinoic acid compounds of the invention.

Anti-proliferative agents that can be used in combination with a retinoic acid compound include, without limitation, microtubule inhibitors, topoisomerase inhibitors, platins, alkylating agents, and anti-metabolites. Particular anty-proliferative agents that are useful in the methods and compositions of the invention include, without limitation, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and vinorelbine. The ability of a compound to inhibit the growth of a neoplasm can be assessed using known animal models.

Compounds which are known to interact with other proteins implicated in Pin1 signaling pathways can also be useful in combination with a retinoic acid compound (see, e.g., the targets and compounds in Table 5).

TABLE 5

| Target | Target Class | Representative Antagonist |
| --- | --- | --- |
| AKT | Kinase | MK-2206 |
| Cyclin D1 | Cyclin | ON 013105 |
| HER2/Neu (ErbB-2) | Kinase | Herceptin |
| NF-☐F | Transcription Factor | RTA 402 |
| Plk | Kinase | BI 2536 |
| Raf-1 | Kinase | Sorafenib |
| Stat3 | Transcription Factor | ISIS-STAT3Rx |
| ☐SIS-STAT | Adhesion | Nucleic Acid-Based Rx in Enzon Program at Santaris |

Such compounds can act synergistically with a retinoic acid compound. Additionally, co-administration with a retinoic acid compound may result in the efficacy of the anti-proliferative compound at lower (and thus safer) doses (e.g., at least 5% less (e.g., at least 10%, 20%, 50%, 80%, 90%, or even 95%) less than when the anti-proliferative compound is administered alone.

Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the patient, the stage and type of the patient's disease, and how the patient responds to the treatment. Additionally, a person having a greater risk of developing an proliferative disease may receive treatment to inhibit or delay the onset of symptoms.

Routes of administration for the various embodiments include, but are not limited to, topical, transdermal, nasal, and systemic administration (such as, intravenous, intramuscular, subcutaneous, inhalation, rectal, buccal, vaginal, intraperitoneal, intraarticular, ophthalmic, otic, or oral administration). As used herein, "systemic administration" refers to all nondermal routes of administration, and specifically excludes topical and transdermal routes of administration.

In combination therapy (e.g., a retinoic acid compound with a second anti-proliferative agent), the dosage and frequency of administration of each component of the combination can be controlled independently. For example, one compound may be administered three times per day, while the second compound may be administered once per day. Alternatively, one compound may be administered earlier and the second compound may be administered later. Combination therapy may be given in on-and-off cycles that include rest periods so that the patient's body has a chance to recover from any as yet unforeseen side effects. The compounds may also be formulated together such that one administration delivers both compounds.

Each compound of the combination may be formulated in a variety of ways that are known in the art. For example, the first and second agents may be formulated together or separately. Desirably, the first and second agents are formulated together for the simultaneous or near simultaneous administration of the agents. Such co-formulated compositions can include the two drugs together in the same pill, ointment, cream, foam, capsule, liquid, etc. It is to be understood that, when referring to the formulation of combinations of the invention, the formulation technology employed is also useful for the formulation of the individual agents of the combination, as well as other combinations of the invention. By using different formulation strategies for different agents, the pharmacokinetic profiles for each agent can be suitably matched.

The individually or separately formulated agents can be packaged together as a kit. Non-limiting examples include kits that contain, e.g., two pills, a pill and a powder, a suppository and a liquid in a vial, two topical creams, ointments, foams etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

IV. Experimental Results

We have identified a series of nanomolar inhibitors that binds only to the catalytically active PPIase domain of Pin1. Upon electroporation or microinjection, these Pin1 peptide inhibitors block HeLa division, and this block is rescued by co-injected Pin1, indicating that the compounds are highly specific and potent. Using the above Pin1 peptide inhibitors, we have developed a high-throughput screen for identifying Pin1 inhibitors using a single-step fluorescence polarization-based displacement assay (FP-HTS). The FP-HTS detects molecules that compete for the substrate binding to the catalytic active site, measures ligand binding under equilibrium conditions, and does not suffer from product inhibition. The HF488 fluorescent probes for the FP assay contain only four residue core structure of Bth-L-phos.Thr-Pip-Nal (pTide), with a Kd of 258 nM for Pin1, was synthesized by Anaspec. We performed FP-HTS in a 384-well plate format with full length Pin1 and produced robust FP, resulting in a 6-7 fold increase in polarization degree values, using a Synergy II plate reader. This novel FP-HTS showed robust and reproducible performance. The assay can tolerate up to 10% DMSO. The Z' is around 0.70 and is consistent for day-to-day performance. The coefficient of variation is in the range of 4-5%. More importantly, we have shown that both pTide, the unlabeled Pin1 peptide as the positive control in this project, and juglone, the Pin1 small molecule inhibitor, displaced HF488 probe from Pin1. Although it is difficult to determine the Kd for the covalent and irreversible inhibitor juglone, the Kd for pTide was ~250 nM, similar to that derived from PPIase-based assays.

Figure 2A:
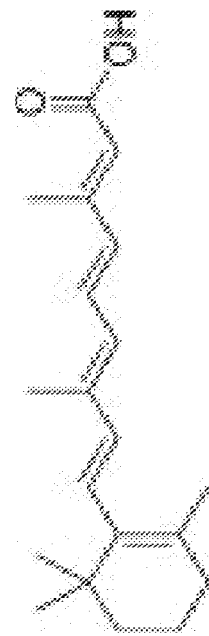
FIG. 2A is a schematic of the chemical structure of 13-cis-retinoic acid and all-trans retinoic acid.
Figure 2A:
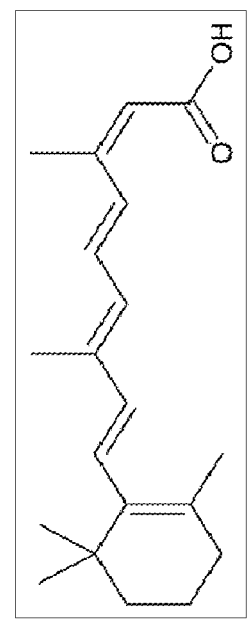
Figure 2B:
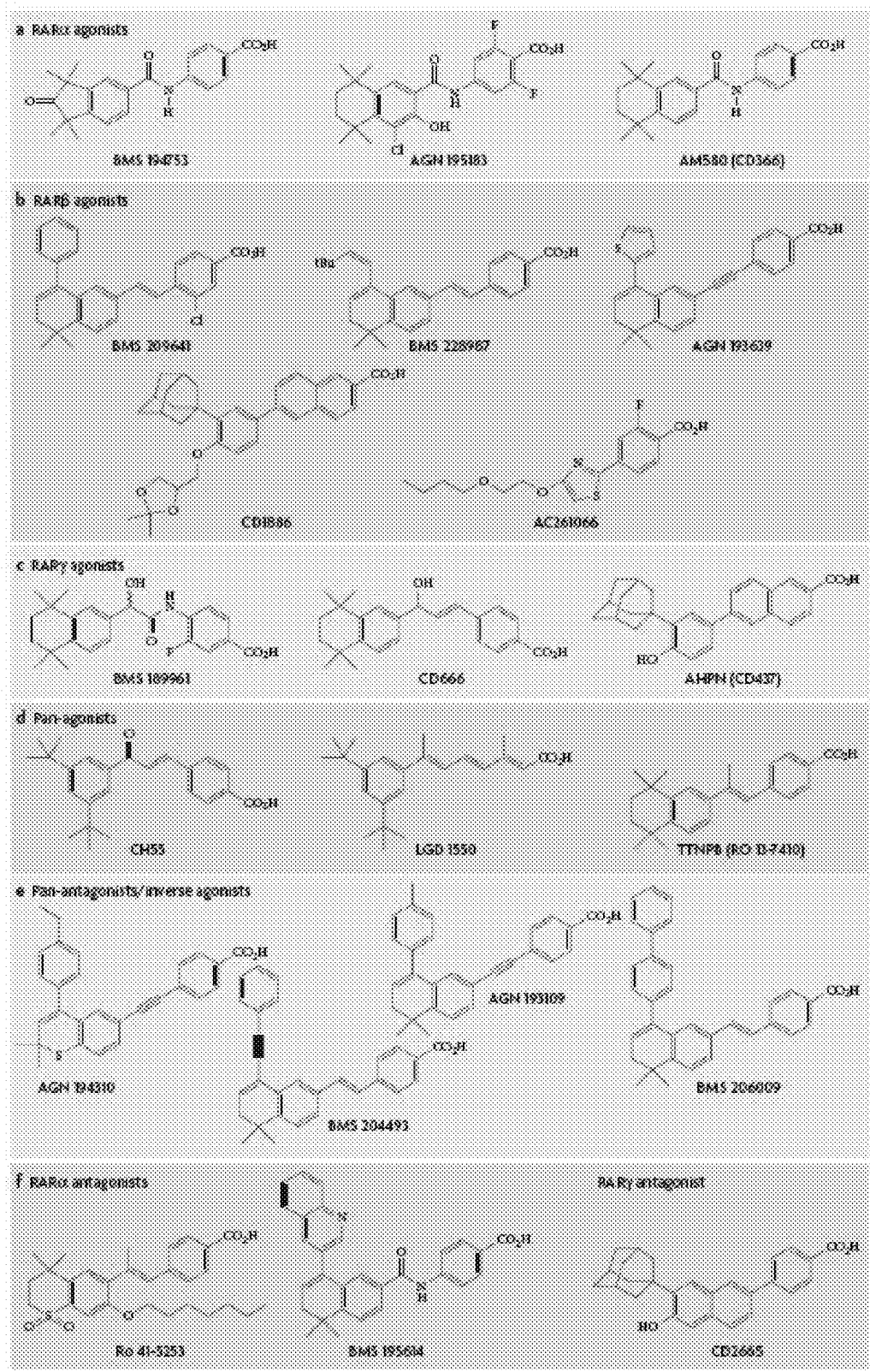
FIG. 2B is a schematic showing additional retinoic acid compounds.
Figure 3:
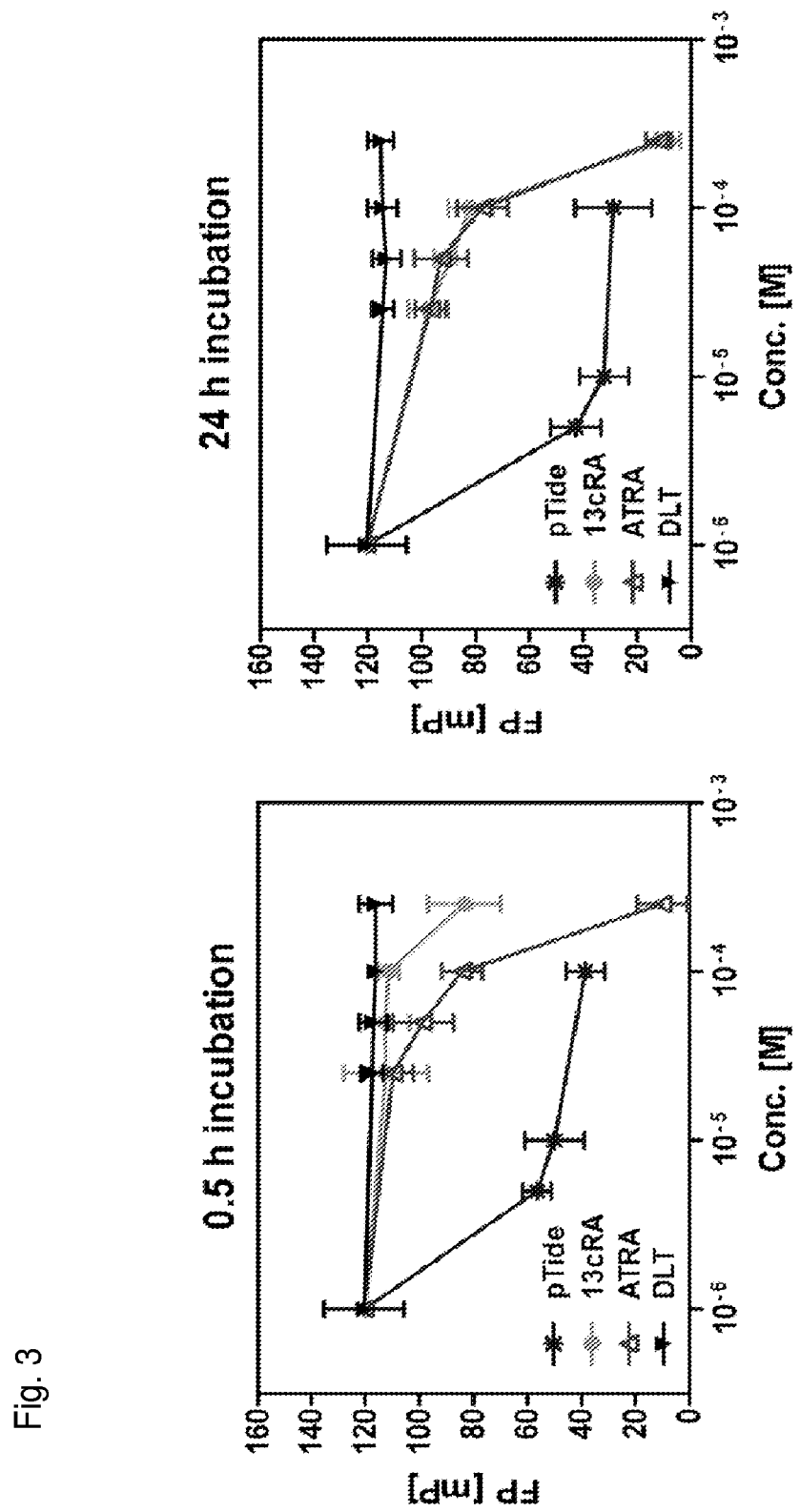
FIG. 3 is a pair of graphs showing the ability of 13-cis-retinoic acid and all-trans retinoic acid at different concentrations to compete with a fluorescence-labeled Pin1 peptide inhibitor probe BIKL-488 for binding Pin1 after an incubation of the indicated amount of time.
Figure 4:
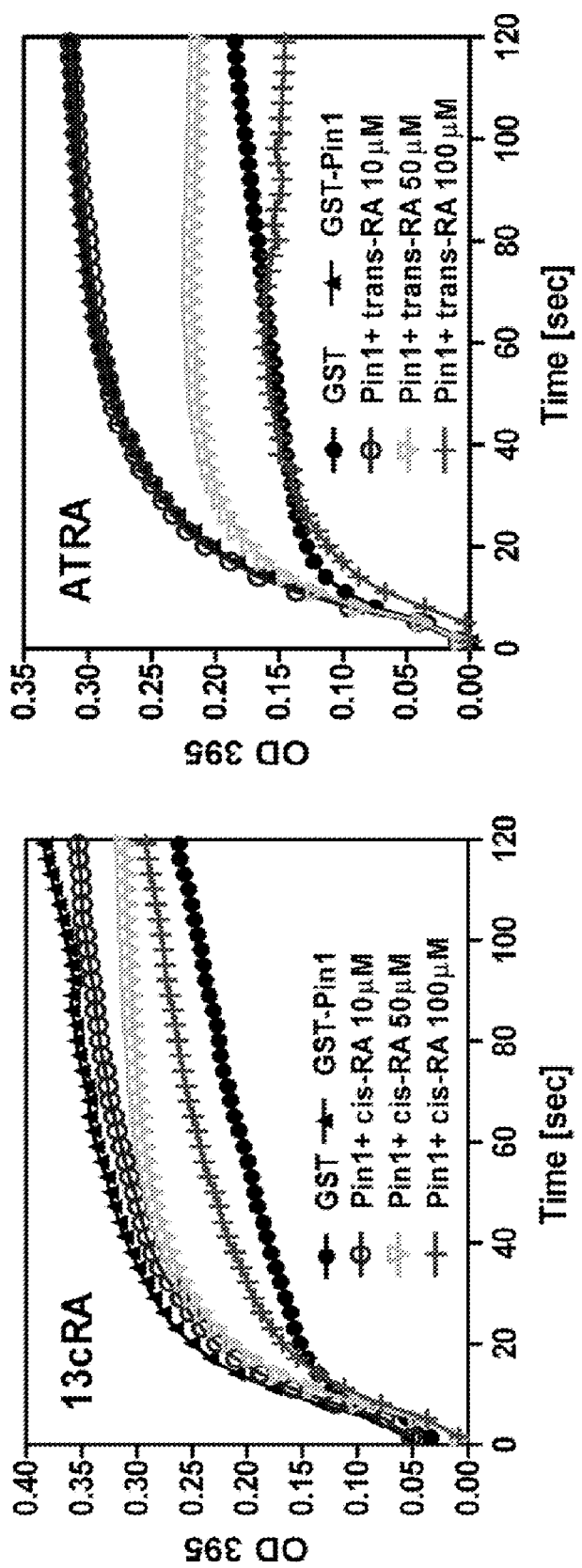
FIG. 4 is a pair of graphs showing inhibition of Pin1 by cis-retinoic acid and trans-retinoic acid at the indicated concentrations.
Figure 5:
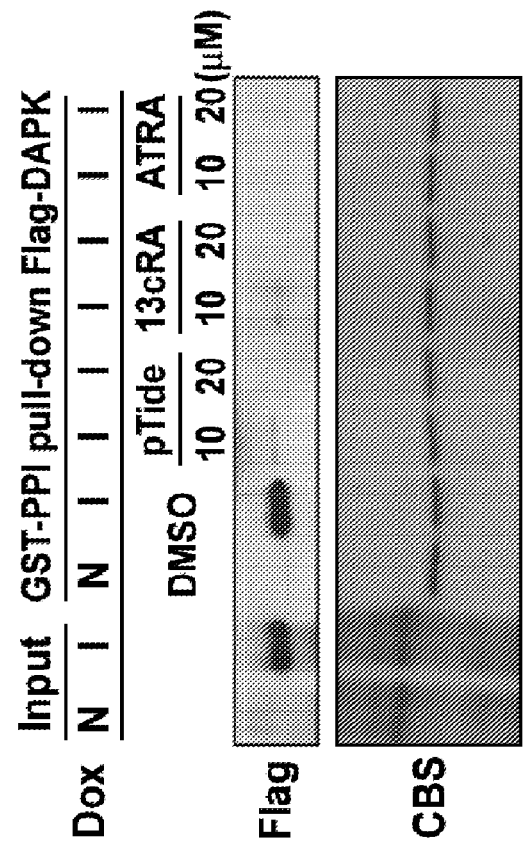
FIG. 5 is a photograph indicating both cis and trans retinoic acids can bind to Pin1 and compete away DAPK, which binds to the Pin1 catalytic domain.
Figure 6:
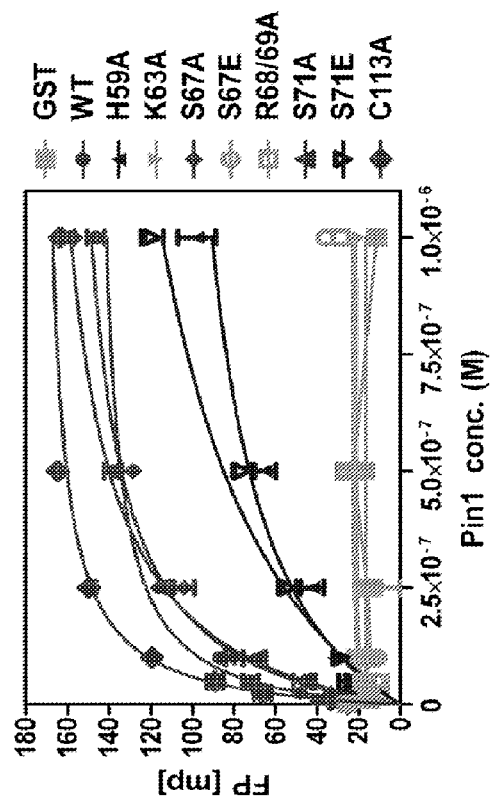
FIG. 6A is a graph showing specific residues in the Pin1 active site that are important for interacting with the detecting probe BIKL-488.
FIG. 6B is a graph showing specific residues in the Pin1 active site that are important for interacting with retinoic acid.
Figure 6:
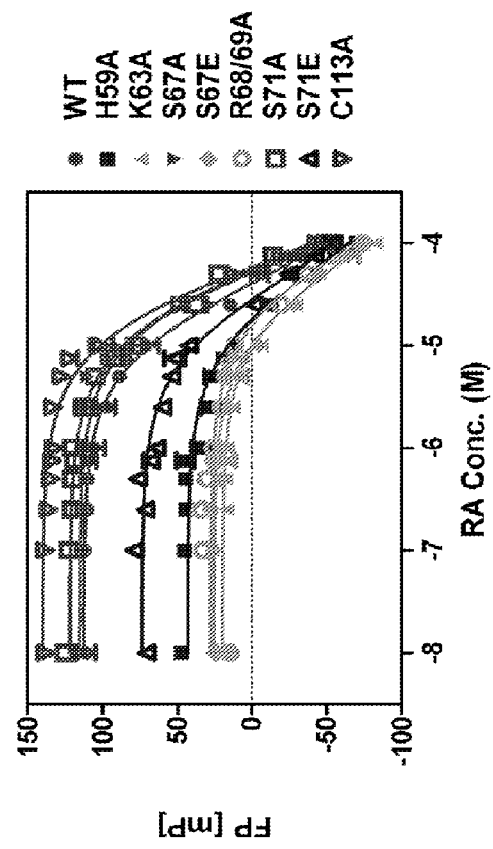

We used the FP-HTS with a 5 nM probe and 200 nM Pin1 to conduct a pilot screen on a selected set of chemical libraries. We obtained the resulting potential positive hits and grouped them into 3 classes according to the Z-score, which is folds of standard deviation below the mean. The top strong chemical is the clinically used drug 13-cis-retinoic acid (cis-RA) (FIG. 2A). cis-RA is particularly attractive for the following reasons. 1) cis-RA is not listed in promiscuous inhibitor databases 2) all-trans retinoic acid (trans-RA), the pairing compound of cis-RA, is currently used as oral prescription for patients with acute promyelocytic leukemia (AML); 3) both cis-RA and trans-RAs are used as a medication in the phase II/III clinical trial for breast cancer, and more because of its ability to kill rapidly dividing cells; and 4) although it has been reported that RAs target on retinoic acid receptor (RAR), the exact mechanism of the anticancer action is unknown. As a result, we examined whether the anti-cancer effect of RAs depends on RAR in the breast cancer cells. RARα knockdown can only partially rescue-cis-RA-mediated cell death, indicating that RAs may have unidentified "off-target effect." To confirm that RAs indeed target Pin1, we examined cis-RA and trans-RA in the FP assay, and, surprisingly, found that trans-RA displayed even more prominent Pin1 inhibition than cis-RA dose and that cis-RA would eventually catch up with trans-RA in the long-term incubation with Pin1, likely due to resonance-mediated cis-trans conversion (FIG. 3). In the PPIase assay, Pin1 activity was blocked by either cis- or trans-RA in a dose-dependent manner (FIG. 4). These data confirm that the interaction between RAs and Pin1 is specific and not due to aggregation. Furthermore, both trans and cis RA blocked the association between Pin1 and DAPK1 in a dose-dependent manner, with trans being more potent (FIG. 5). These results indicate that RAs binds to Pin1 C-terminal catalytic domain because DAPK1 is known to bind this domain (Lee et al., 2011 Mol Cell in press). To determine which amino acid residue in the Pin1 catalytic domain that are important for retinoic acid binding, point mutations of Pin1 including K63A, S67E, R68/69A, H59A or S71E completely or significantly abolished trans-RA binding to Pin1 (FIGS. 6A and B). Together, these data indicate that RAs inhibit Pin1 by occupying its catalytic PPIase pocket in the C-terminus and that phosphorylation of Ser67 or Ser71 inhibits RA binding to Pin1.

Figure 7:
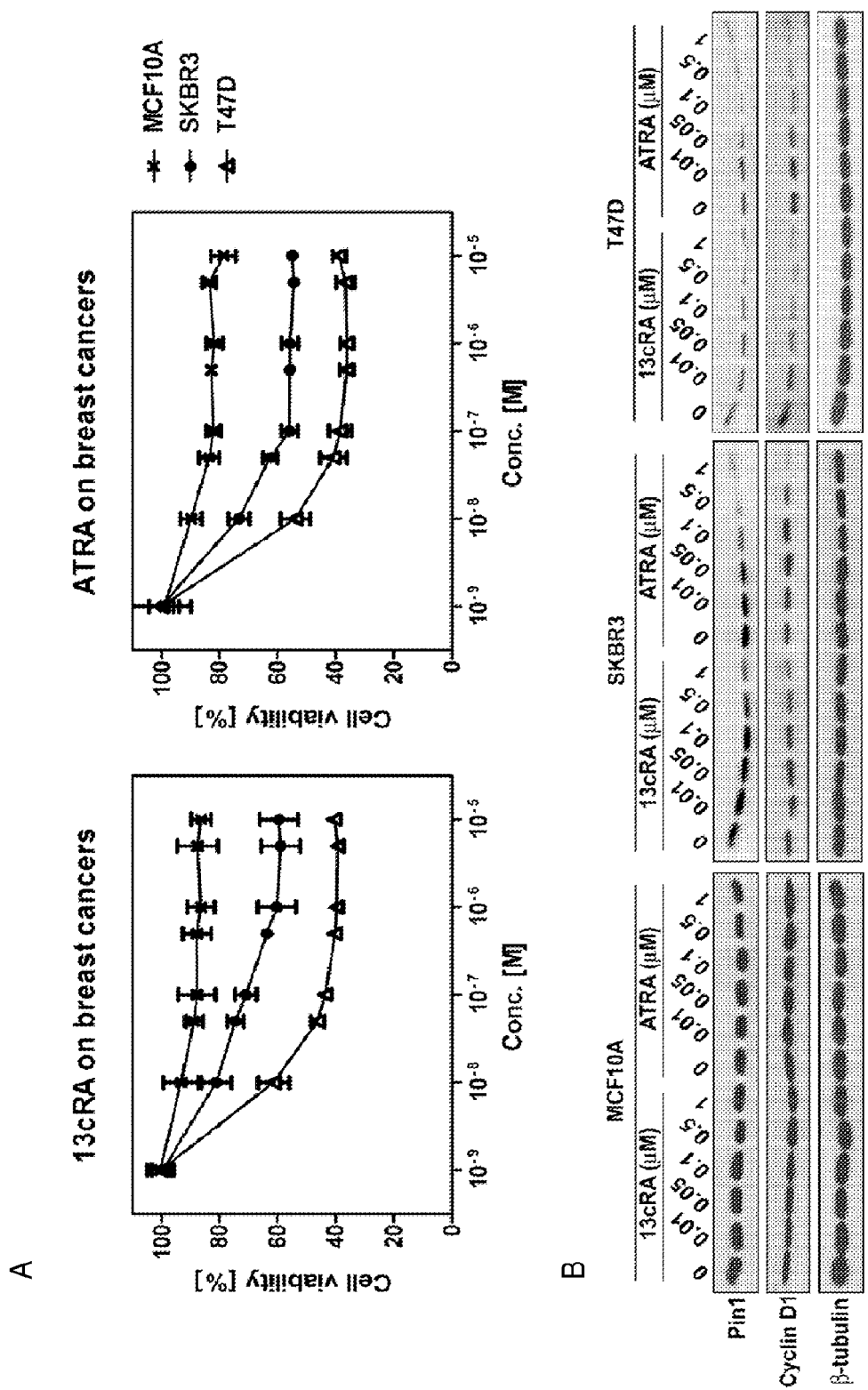
FIG. 7A is a pair of graphs showing cell viability of the indicated cell lines as a function of concentration of cis-retinoic acid or trans-retinoic acid.
FIG. 7B is a series Western blots showing expression of the indicated protein in cells treated with of either cis-retinoic acid or trans-retinoic acid in the indicated cell lines.
Figure 8:
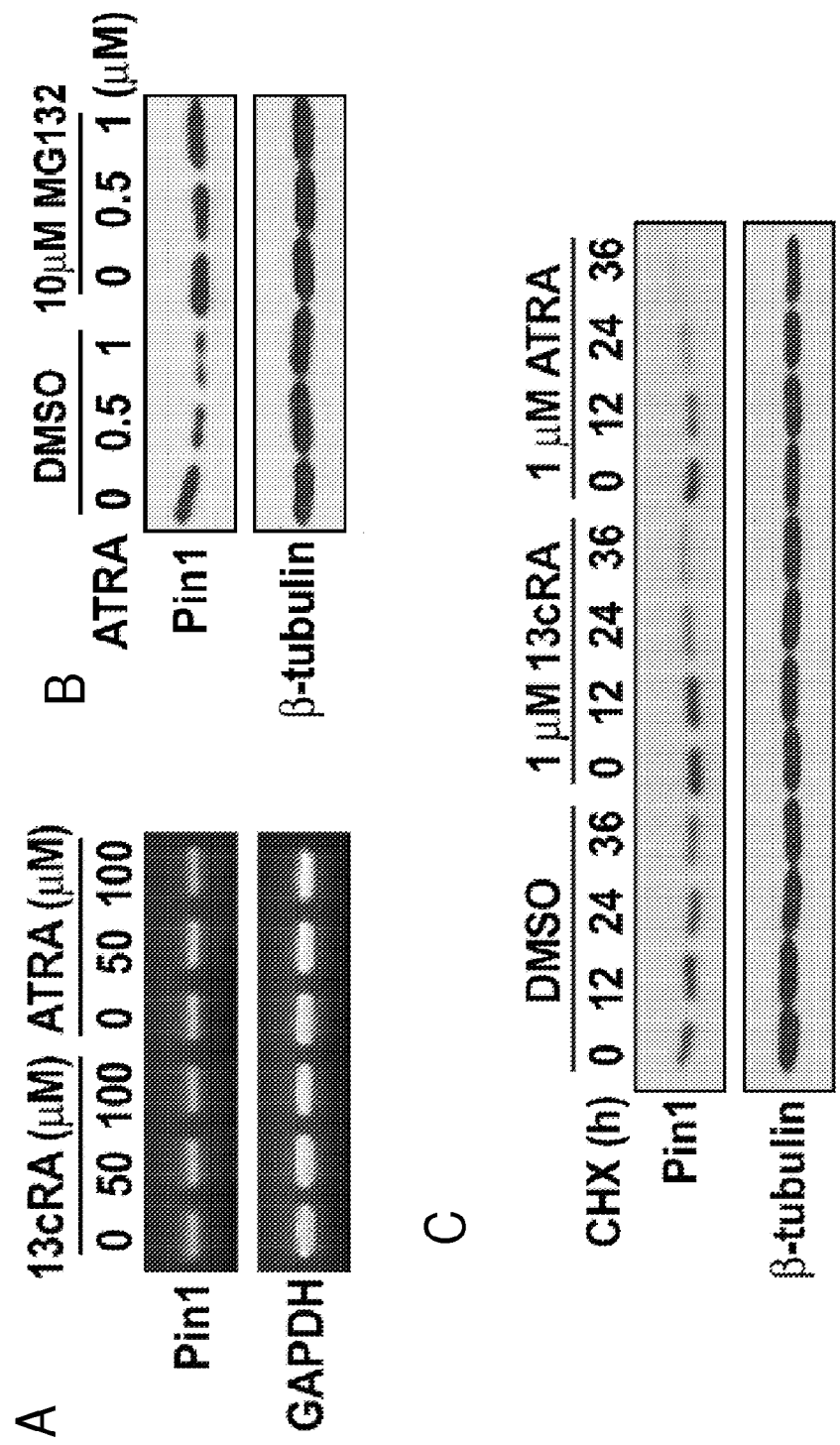
FIG. 8A is a photograph indicating the amount of Pin1 or GAPDH mRNA produced in the presence of the indicated compound as measured in an RT-PCR experiment.
FIG. 8B is a Western blot showing Pin1 and tubulin protein levels in cells treated with the indicated compounds.
FIG. 8C is a Western blot showing Pin1 and tubulin protein levels in cells treated with cycloheximide and the indicated compound.
Figure 9:
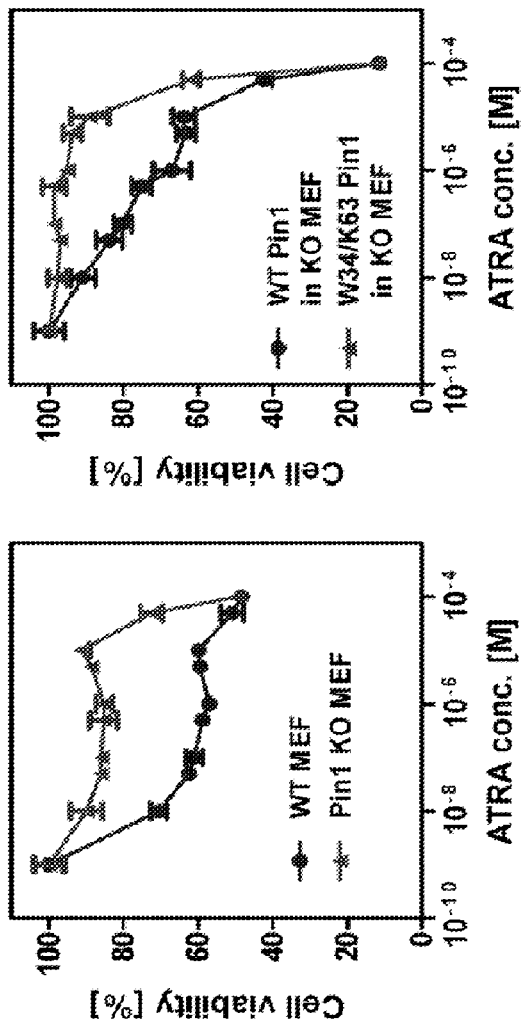
FIG. 9A is a pair of graphs showing cell viability as a function of the concentration of all trans-retinoic acid in the indicated cell types.
FIG. 9B is a Western blot showing Pin1 protein levels in the indicated cell types.
FIG. 9C is Western blot showing Pin1 protein levels in the indicated cell types treated with either 13cRA or ATRA.
Figure 9:
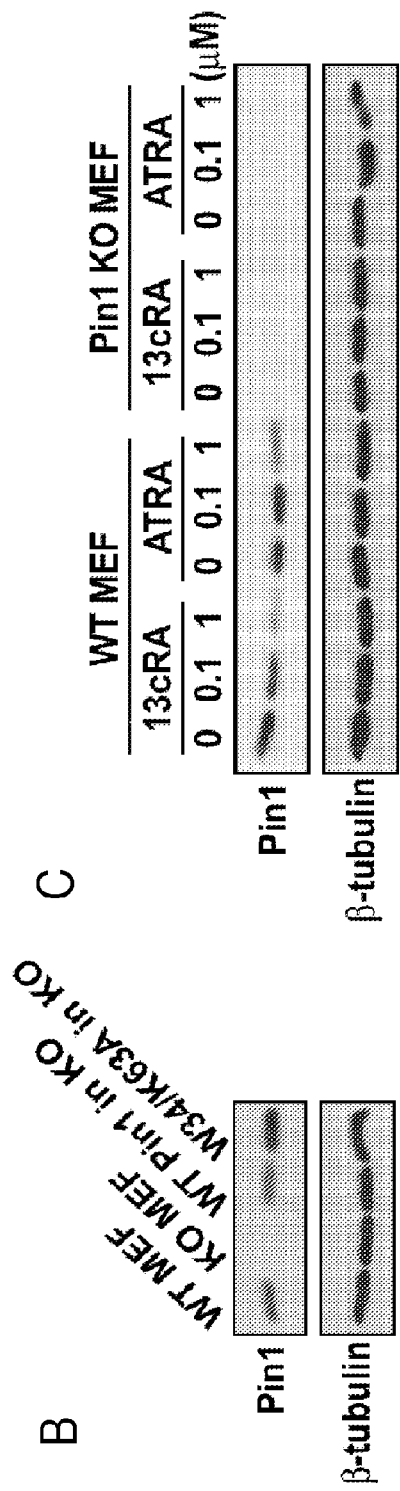

To further discern the causal relationship between the anti-proliferative effect of RAs on Pin1, cell viability of three breast cancer cell lines was tested with different dosages of cis- or trans-RA, of which SKBR3 and T47D exhibited preferential sensitivity to RAs with an IC50 in the nano-molar range, while the normal cell line MCF10A remained unaffected (FIG. 7A). This discrepancy between cell lines was correlated with the RAs' ability to suppress Pin1 expression. Pin1 level was decreased by treatment of RAs in drugs-responsive SKBR3 and T47D, but not in drugs-irresponsive normal cells, MCF10A (FIG. 7B), in which Pin1 target protein, cyclin D1, was served as biomarkers of in vivo Pin1 activity. Moreover, RAs did not alter Pin1 mRNA level, but did reduce Pin1 protein stability, suggesting that RAs interact with Pin1, result in Pin1 degradation, and subsequently leads to anti-proliferation of breast cancer cells (FIGS. 8A-C). To further confirm this premise, wild-type mouse embryonic fibroblast (WT MEF) and Pin1 knockout MEF (Pin1 KO MEF) were used to test trans-RA-mediated cell viability (FIGS. 9A-C). As expected, Pin1 KO MEF was more resistant to trans-RA than WT MEF due to lack of drug target. In addition, Pin1 KO MEF stably expressing WT Pin1, but not W34/K63A Pin1 mutant, enabled cells to re-sensitize trans-RA. These results indicate that RAs-mediated cell death is at least in part dependent on Pin1.

Figure 10:
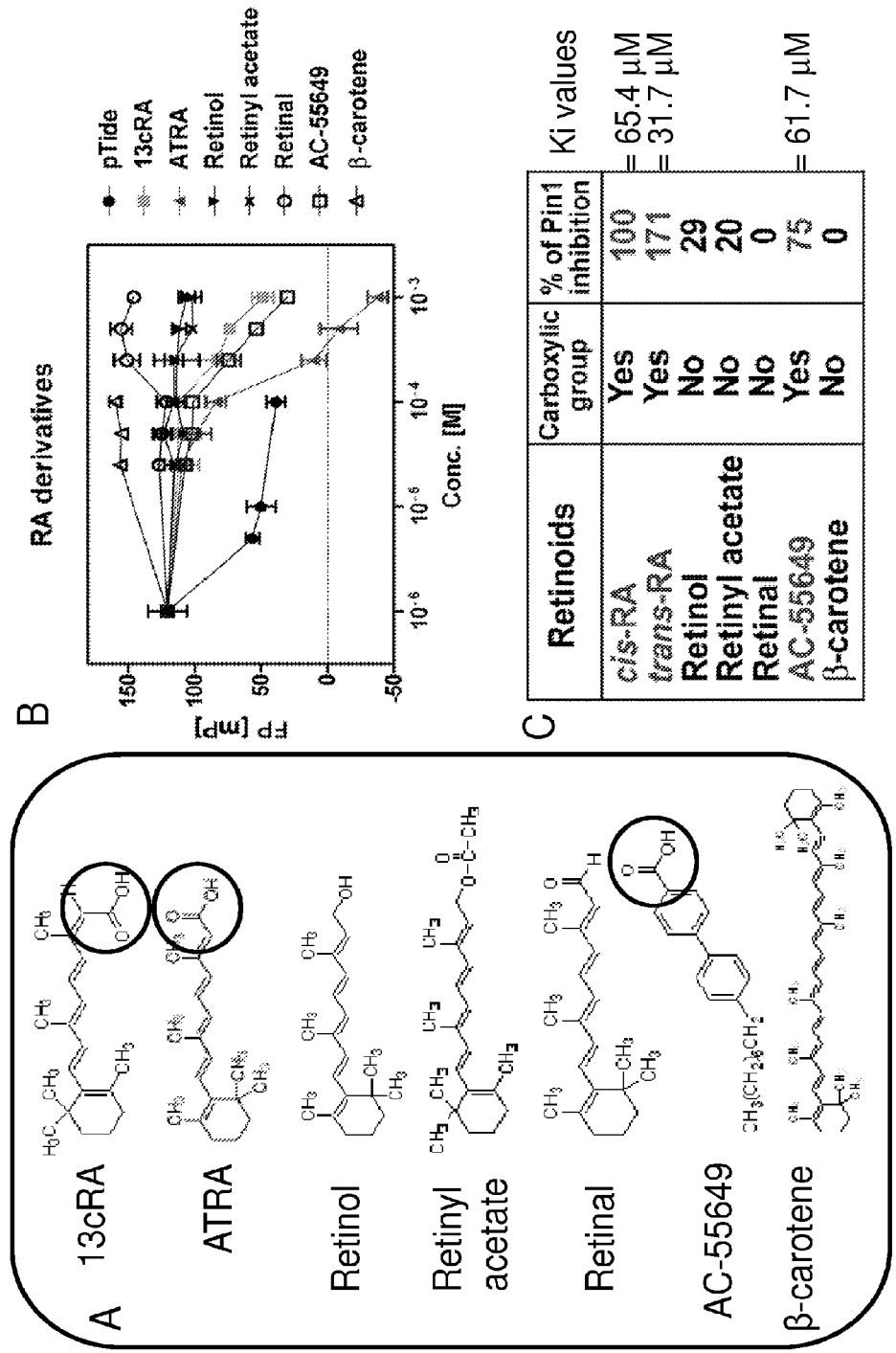
FIG. 10A is a series of schematics showing the indicated retinoic acid compounds and β-carotene.
FIG. 10B is a graph showing the concentration of free particles of Pin1 as a function of concentration of the indicated compounds.
FIG. 10C is a table summarizing the results of FIG. 10B.
FIG. 10D is a series of schematics showing compounds that modulate the retinoic acid receptor.
Figure 10:
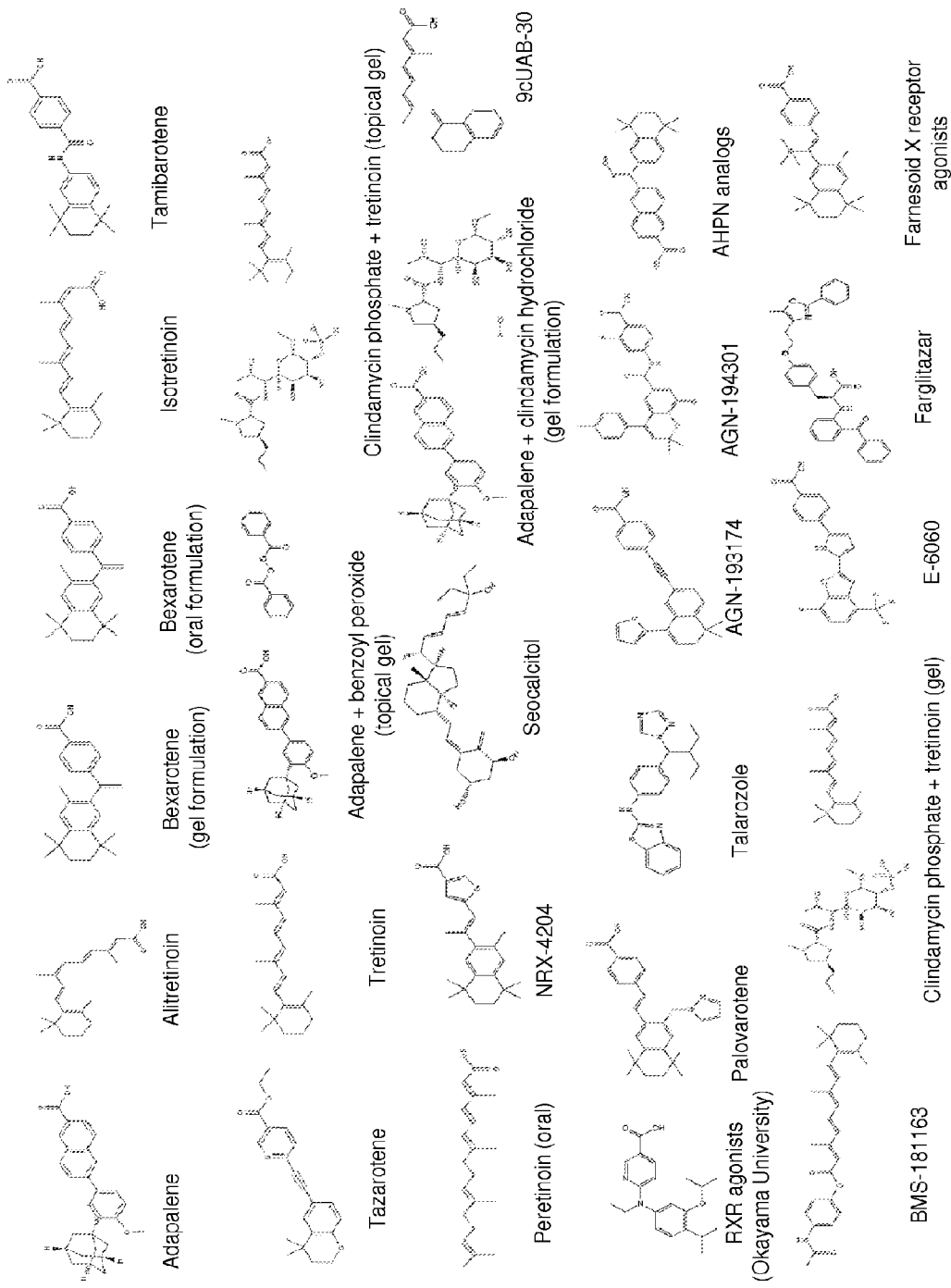
Figure 10:
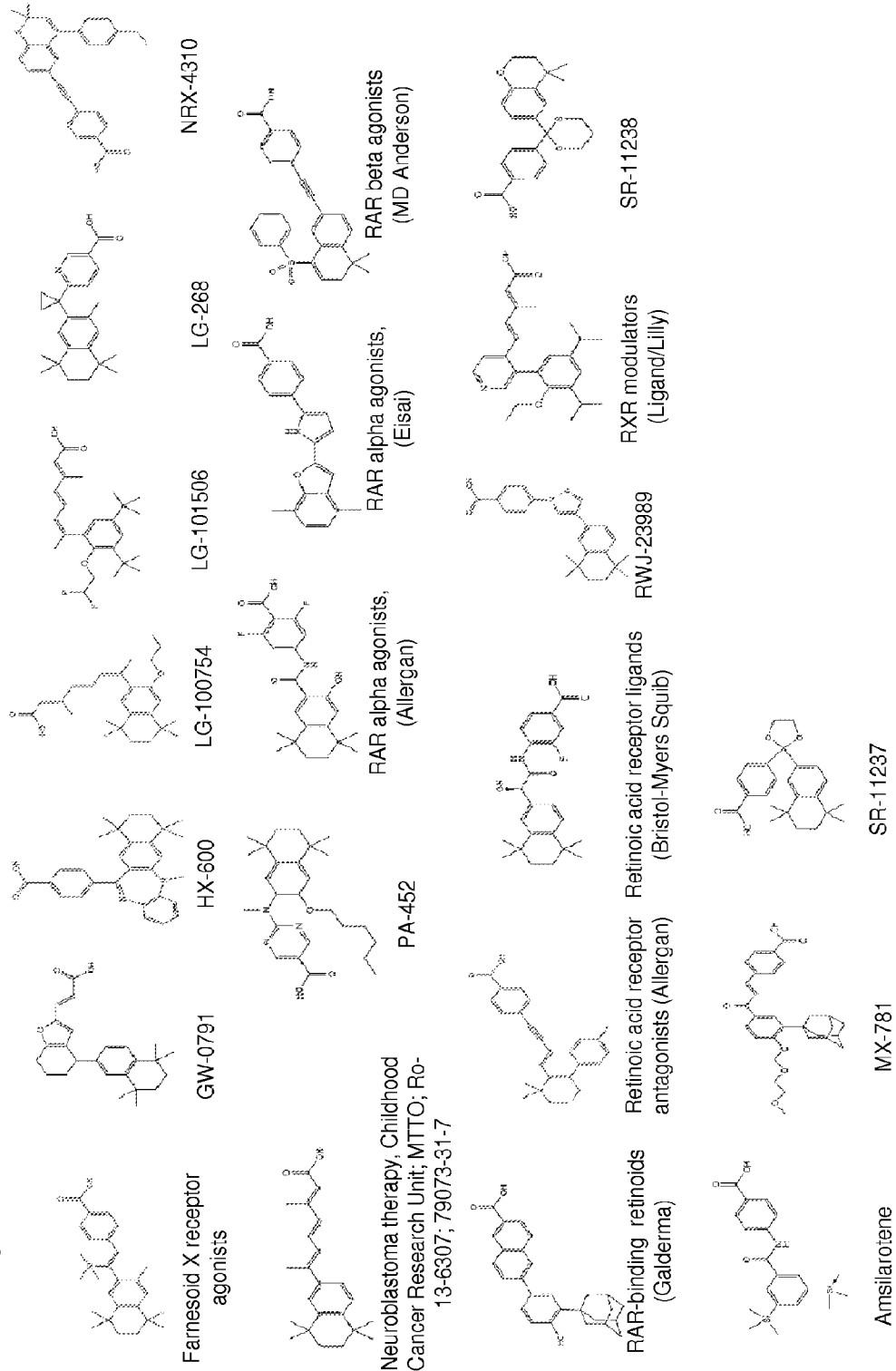
Figure 11:
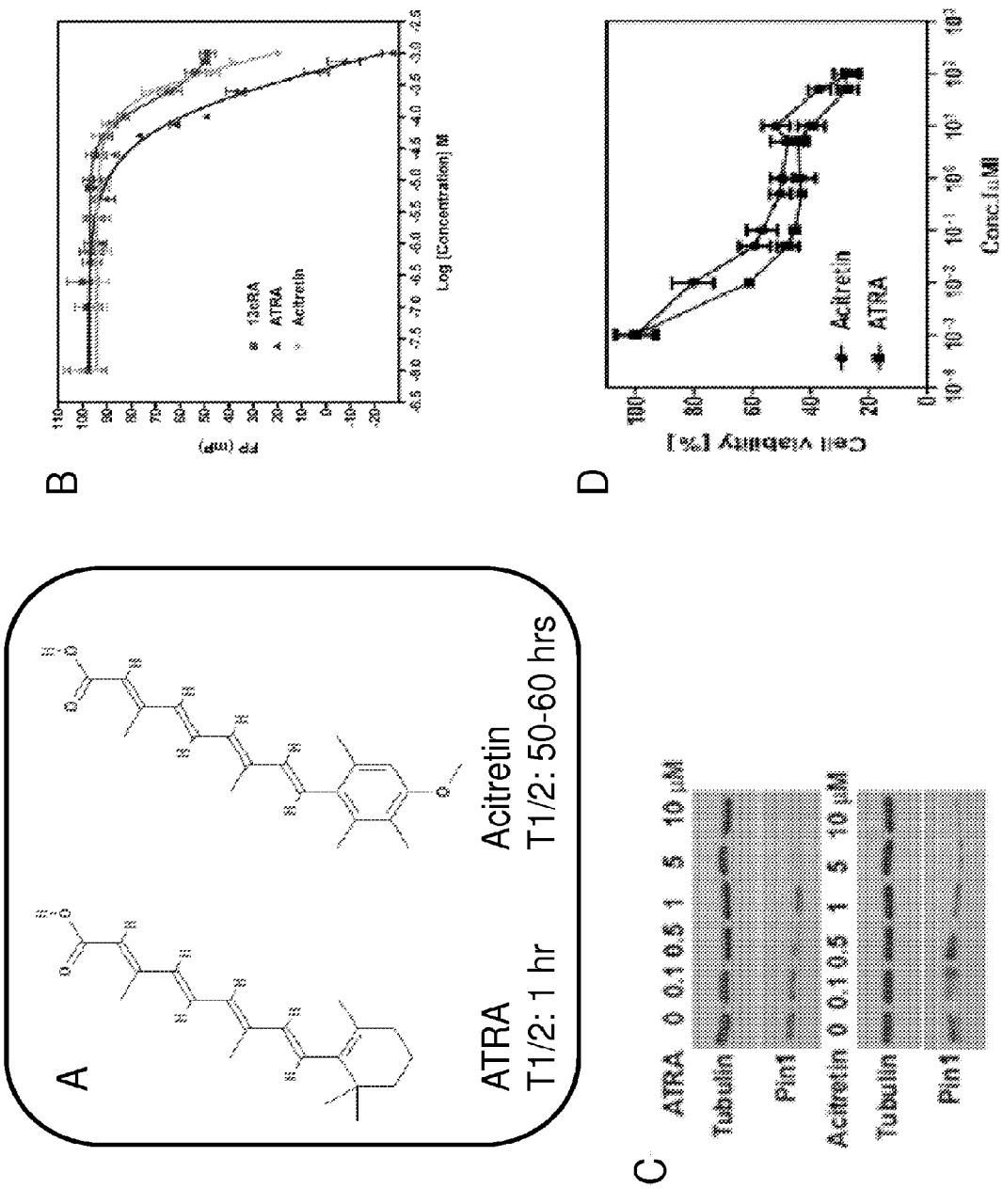
FIG. 11A is a schematic of the chemical structure of all-trans retinoic acid and acitretin.
FIG. 11B is a graph showing the concentration of free particles of Pin1 as a function of concentration of the indicated compounds.
FIG. 11C is a Western blot showing Pin1 and tubulin protein levels in cells treated with the different concentrations of the indicated compound.
FIG. 11D is a graph showing cell viability as a function of the concentration of the indicated compounds.

As trans-RA is selected as the current lead compound, it is important to identify the essential moiety of RAs on Pin1 interaction for further lead optimization. Many commercially available retinoids were tested for Pin1 inhibition. Only those with end carboxylic group maintained Pin1 inhibition in a cell culture model, which are cis-RA, trans-RA, AC-55649, and acitretin (FIGS. 10A, 10B, 11A, and 11B). Other RA compounds that are metabolized to contain an end carboxylic group are also likely to be useful in treating proliferative disorders (FIG. 10D). In addition, compounds that modulate the retinoic acid receptor (FIGS. 10D and 11A and compounds listed in Table 1) are also likely to be useful in treating proliferative disorders.

In addition, we have developed Cell-based assays to screen and validate Pin1 inhibitor hits. We have shown 1) that Pin1 is highly expressed in HER2-positive human breast cancer tissues; 2) that Pin1 inhibition almost completely suppresses HER2 overexpression on cell surface in human HER2+ breast cancer cell lines such as AU565 and SKBR3 cells; 3) that Pin1 inhibition greatly increases the sensitivity of HER2+ breast cancer cells to the mTOR inhibitor, but not to the HER2 inhibitor, suggesting that Pin1 might act on Her2 to regulate cell growth; 4) that Pin1 acts on Neu and multiple substrates in Neu-mediated oncogenic pathway; and 5) that Pin1 knockout in mice inhibits breast cancer development induced by activated Her2. Therefore, Pin1 is essential for maintaining HER2 overexpression and growth of human HER2+ breast cancer cells. Given that HER2 expression on cell surface and cell growth are readily assayed on 384-well format, we can test the ability of the hits to repress HER2 overexpression and cell growth of HER2_AU565 and SKBR3 cells, which will be treated with Pin1 prodrugs or hits, and then immunostained with Alexa 488-anti-HER2 monoclonal antibody (BioLegend), followed by automated microscopy.

Figure 12:
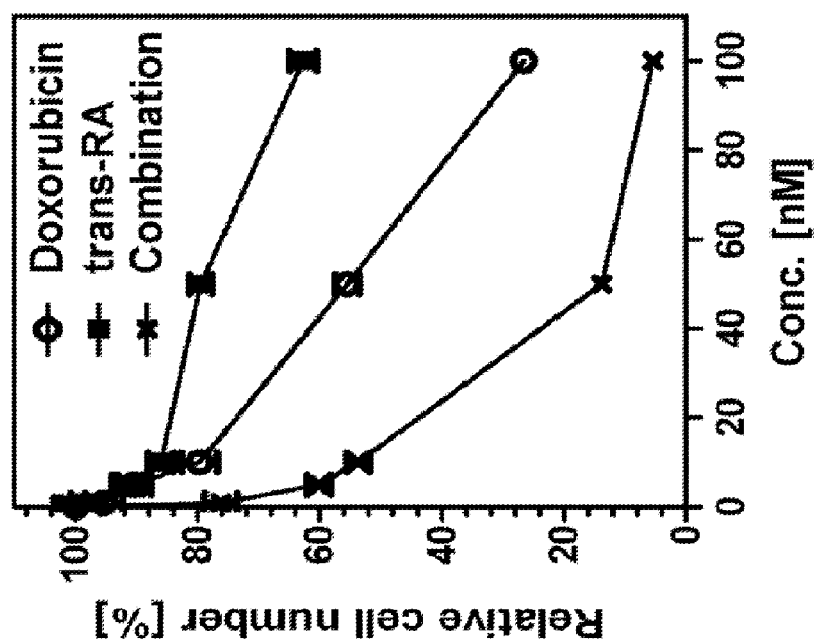
FIG. 12 is a graph showing cell number as a function of the concentration of the indicated compound or combination of compounds. For data points corresponding to the combination of compounds, the concentration value corresponds to the concentration of each individual compound in the combination.

We have further shown that combinations of therapeutic compounds including retinoic acid compounds are useful for treating cancer, e.g., cancer characterized by elevated Pin1 activity. FIG. 12 shows results obtained from the treatment of breast cancer cells overexpressing Pin1 with ATRA or Doxorubicin or their combination, followed by counting cancer cell numbers. The results show that ATRA and Doxorubicin combination dramatically increases anticancer potency and reduce the dose of each drug to inhibit cancer cell growth. Therefore, ATRA can drastically reduce dose and toxicity of Doxorubicin and other chemotherapeutic drugs.

Figure 13:
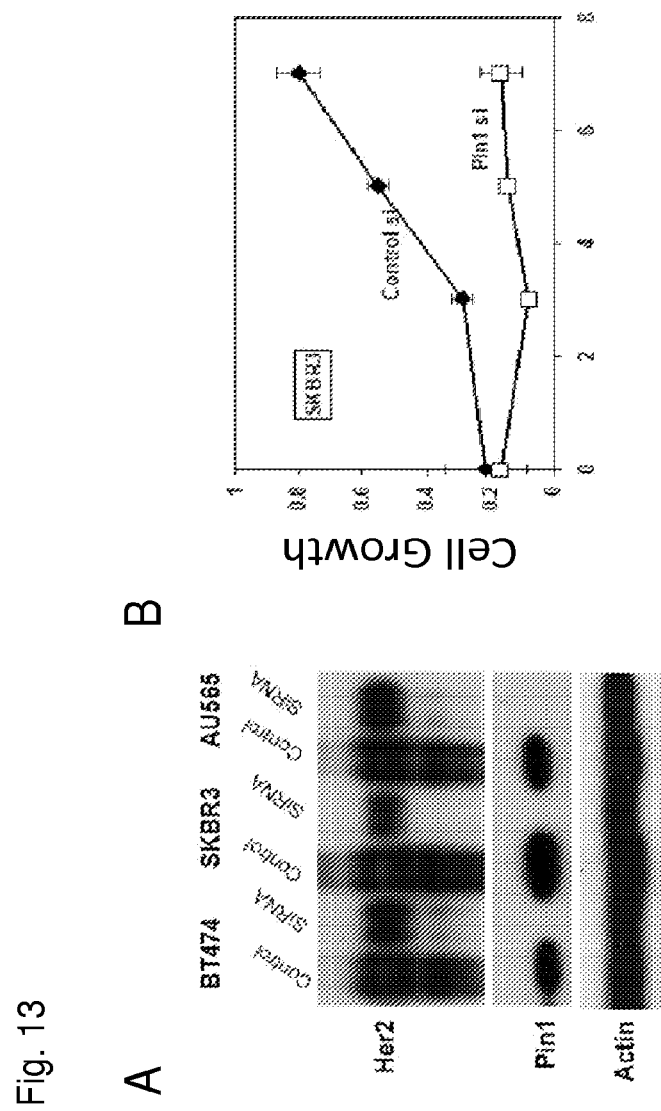
FIG. 13A is a Western blot showing Pin, Her2, and actin protein levels in human breast cancer cells treated with the siRNA to inhibit Pin1.
FIG. 13B is a graph showing cell number as a function of inhibiting Pin1 in cells by siRNA.

We have also shown that Pin1 inhibition, using siRNA, dramatically reduces Neu/Erb2 overexpression and cell proliferation of human breast cancer cells that have Neu/Erb2 gene amplification (FIGS. 13A and 13B). This provides us with a method to identify a Pin1 modulatory compound by applying a test compound to human-derived cancer cells that have Neu/Erb2 gene amplification, and determining the effect of the test compound on Neu/Erb2 overexpression and cell proliferation.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of treating a cancer or leukemia in a subject with the cancer or leukemia, respectively, said method comprising:
   (a) performing an assay to identify the subject as having an elevated level of Pin1 in the cells of the cancer relative to non-cancerous cells of the same tissue type: and
   (b) administering to said subject a pharmaceutical composition comprising:
      (i) an effective amount of a retinoic acid compound, and
      (ii) one or more additional therapeutic agents,
   wherein the retinoic acid compound is administered to the subject as the sole Pin1 inhibitor and in an amount that reduces Pin1 activity in the cells of the cancer or leukemia by 30% or more relative to a subject not administered the retinoic acid compound, and wherein said retinoic acid compound, but not said one or more additional therapeutic agents, is formulated for controlled or extended release.

2. The method of claim 1, wherein the rate of release of said retinoic acid compound exceeds the rate of metabolism of said retinoic acid compound.

3. The method of claim 1, wherein said retinoic acid compound is released at period intervals.

4. The method of claim 1, wherein said pharmaceutical composition is formulated as a single unit tablet, multiple unit tablet, capsule, oil solution, suspension, emulsion, microcapsule, microsphere, nanoparticle, or patch.

5. The method of claim 1, wherein said pharmaceutical composition comprises one or more liposomes comprising said retinoic acid compound.

6. The method of claim 1, wherein said one or more additional therapeutic agents comprises one or more antiproliferative agents.

7. The method of claim 1, wherein said pharmaceutical composition is formulated such that the release of said retinoic acid compound and said one or more additional therapeutic agents is simultaneous.

8. The method of claim 1, wherein said pharmaceutical composition is formulated such that said retinoic acid compound is released prior to said one or more additional therapeutic agents.

9. The method of claim 1, wherein said pharmaceutical composition is formulated such that said retinoic acid compound is released after said one or more additional therapeutic agents.

10. The method of claim 1, wherein said retinoic acid compound is all-trans retinoic acid.

11. The method of claim 1, wherein said cancer or leukemia is selected from the group consisting of: acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemi), Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

12. The method of claim 11, wherein said cancer or leukemia is breast cancer.

13. The method of claim 1, wherein said pharmaceutical composition and said one or more therapeutic agents are administered separately or in a single formulation.

14. A method of treating a cancer or leukemia in a subject with the cancer or leukemia, respectively, said method comprising:
   (a) performing an assay to identify the subject as having an elevated level of Pin1 in the cells of the cancer relative to non-cancerous cells of the same tissue type: and administering to said subject a pharmaceutical composition comprising:
(i) an effective amount of a retinoic acid compound, and
(ii) a second therapeutic agent selected from the group consisting of a microtubule inhibitor, a topoisomerase inhibitor, a platin, an alkylating agent, an anti-metabolite, an AKT antagonist, a cyclin D1 antagonist, a HER2 antagonist, an NF-kB antagonist, a Plk antagonist, a Raf-1 antagonist, a Stat3 antagonist, and an ISIS-STAT antagonist;
wherein the retinoic acid compound is administered to the subject as the sole Pin1 inhibitor and in an amount that reduces Pin1 activity in the cells of the cancer or leukemia by 30% or more relative to a subject not administered the retinoic acid compound, and wherein said pharmaceutical composition is formulated for controlled or extended release.

15. A method of treating a cancer or leukemia in a subject with the cancer or leukemia, respectively, said method comprising:
(a) performing an assay to identify the subject as having an elevated level of Pin1 in the cells of the cancer relative to non-cancerous cells of the same tissue type: and
(b) administering to said subject having elevated levels of Pin1 activity
a pharmaceutical composition comprising:
(i) an effective amount of a retinoic acid compound, and
(ii) a second therapeutic agent selected from the group consisting of MK-2206, ON 013105, Herceptin, RTA 402, B12536, Sorafenib, ISIS-STAT3Rx, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and vinorelbine;
wherein the retinoic acid compound is administered as the sole Pin1 inhibitor and in an amount that reduces Pin1 activity in the cells of the cancer or leukemia by 30% or more relative to a subject not administered the retinoic acid compound, and wherein said pharmaceutical composition is formulated for controlled or extended release.

16. The method of claim 1, wherein said retinoic acid is administered in an amount sufficient to reduce the Pin1 activity in the cells of said cancer by 50% or more relative to a subject not administered said retinoic acid compound.

17. The method of claim 16, wherein said retinoic acid is administered in an amount sufficient to reduce the Pin1 activity in the cells of said cancer by 90% or more relative to a subject not administered said retinoic acid compound.

18. The method of claim 14, wherein said retinoic acid compound is administered in an amount sufficient to reduce the Pin1 activity in the cells of said cancer by 50% or more relative to a subject not administered said retinoic acid compound.

19. The method of claim 15, wherein said retinoic acid compound is administered in an amount sufficient to reduce the Pin1 activity in the cells of said cancer by 50% or more relative to a subject not administered said retinoic acid compound.

* * * * *

UNITED STATES PATENT AND TRADEMARK OFFICE
CERTIFICATE OF CORRECTION

PATENT NO.        : 10,265,288 B2
APPLICATION NO.   : 14/334052
DATED             : April 23, 2019
INVENTOR(S)       : Kun Ping Lu et al.

Page 1 of 1

It is certified that error appears in the above-identified patent and that said Letters Patent is hereby corrected as shown below:

In the Claims

Column 50, Line 37, replace "leukemi" with --leukemia--.

Column 51, Line 10, replace "NF-kB" with --NF-κB--.

Signed and Sealed this
Eighth Day of October, 2019

Andrei Iancu
*Director of the United States Patent and Trademark Office*